(12) United States Patent
Schaffer et al.

(10) Patent No.: US 11,530,421 B2
(45) Date of Patent: Dec. 20, 2022

(54) SELF-INACTIVATING ENDONUCLEASE-ENCODING NUCLEIC ACIDS AND METHODS OF USING THE SAME

(71) Applicant: The Regents of the University of California, Oakland, CA (US)

(72) Inventors: David V. Schaffer, Danville, CA (US); Benjamin Ezra Epstein, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 702 days.

(21) Appl. No.: 16/068,011

(22) PCT Filed: Jan. 31, 2017

(86) PCT No.: PCT/US2017/015812
§ 371 (c)(1),
(2) Date: Jul. 3, 2018

(87) PCT Pub. No.: WO2017/136335
PCT Pub. Date: Aug. 10, 2017

(65) Prior Publication Data
US 2020/0149064 A1 May 14, 2020

Related U.S. Application Data

(60) Provisional application No. 62/289,645, filed on Feb. 1, 2016.

(51) Int. Cl.
| | | |
|---|---|---|
| *C12N 9/22* | (2006.01) |
| *C12N 15/86* | (2006.01) |
| *C12N 7/00* | (2006.01) |
| *C12N 15/11* | (2006.01) |

(52) U.S. Cl.
CPC .............. *C12N 15/86* (2013.01); *C12N 7/00* (2013.01); *C12N 9/22* (2013.01); *C12N 15/11* (2013.01); *C12N 2310/20* (2017.05); *C12N 2750/14143* (2013.01); *C12N 2800/80* (2013.01)

(58) Field of Classification Search
CPC ...... C12N 15/86; C12N 9/22; C12N 2310/20; C12N 2800/80
See application file for complete search history.

(56) References Cited

FOREIGN PATENT DOCUMENTS

WO WO 2015/089351 A1 6/2015

OTHER PUBLICATIONS

Moore, et al.; "CRISPR-based self-cleaving mechanism for controllable gene delivery in human cells"; Nucleic Acids Research; vol. 43, No. 2, pp. 1297-1303 (2015).

*Primary Examiner* — Maryam Monshipouri
(74) *Attorney, Agent, or Firm* — Bozicevic Field & Francis, LLP; Paula Borden; Mandar Joshi

(57) ABSTRACT

Disclosed herein is a functional nucleic acid that includes i) one or more coding nucleotide sequences encoding a genome editing endonuclease; ii) regulatory sequences operably linked to the one or more coding nucleotide sequences; and iii) one or more genome editing endonuclease-recognized sequences, wherein the functional nucleic acid is configured to express the endonuclease in a host cell and thereby provide a cellular endonuclease activity in a sequence-specific manner in the host cell, and wherein cleavage of the functional nucleic acid by the endonuclease inactivates the cellular endonuclease activity. Methods of using the present functional nucleic acid, and systems and kits that find use in performing the same are also provided.

11 Claims, 9 Drawing Sheets
Specification includes a Sequence Listing.

SELF-INACTIVATING ENDONUCLEASE-ENCODING NUCLEIC ACIDS AND METHODS OF USING THE SAME

CROSS-REFERENCE

This application is a national stage filing under 35 U.S.C. § 371 of PCT/US2017/015812, filed Jan. 31, 2017, which claims the benefit of U.S. Provisional Patent Application No. 62/289,645, filed Feb. 1, 2016, which applications are incorporated herein by reference in their entirety.

STATEMENT REGARDING FEDERALLY SPONSORED RESEARCH

This invention was made with government support under Grant Nos. EY022975 and GM098218 awarded by the National Institutes of Health. The government has certain rights in the invention.

INCORPORATION BY REFERENCE OF SEQUENCE LISTING PROVIDED AS A TEXT FILE

A Sequence Listing is provided herewith as a text file, "BERK-313PRV (UC 2016-029) seqlist_ST25.txt" created on Jan. 26, 2016 and having a size of 7,879 KB. The contents of the text file are incorporated by reference herein in their entirety.

INTRODUCTION

Sequence-specific endonucleases are DNA-cleaving enzymes that recognize a target nucleic acid by binding to a target sequence in the target nucleic acid creating double-stranded breaks (DSBs) or single-stranded nicks in the target nucleic acid upon binding. In cells, the creation of DSBs or knicks trigger a cellular repair response, such as base excision repair (BER), nucleotide excision repair (NER), non-homologous end joining (NHEJ), microhomology-mediated end joining (MMEJ), and homologous recombination.

The advent of highly "engineerable" custom endonucleases that can be targeted against specific sites in a genome, such as zinc-finger nucleases (ZFNs), transcription activator-like effector nucleases (TALEN®s), and the clustered regularly interspaced short palindromic repeats (CRISPR)/CRISPR associated protein 9 (Cas9) system, has opened the door to a wealth of possibilities in the field of genome editing in biology and medicine. Among such possibilities is the therapeutic use of gene editing technology to correct the causes of human genetic disease.

SUMMARY

Provided herein is a functional nucleic acid that encodes a genome editing endonuclease that cleaves a nucleic acid at a target sequence, e.g., a target genomic sequence, where the functional nucleic acid contains the target sequence of the endonuclease, such that a genome editing endonuclease expressed by the functional nucleic acid can cleave the functional nucleic acid and prevent further expression of the genome editing endonuclease from the cleaved functional nucleic acid.

The present functional nucleic acid may include i) one or more coding nucleotide sequences encoding a sequence-specific endonuclease; ii) regulatory sequences operably linked to the one or more coding nucleotide sequences; and iii) one or more endonuclease-recognized sequences, wherein the endonuclease-recognized sequences render the functional nucleic acid cleavable by the endonuclease in a cellular context, wherein the functional nucleic acid is configured to express the endonuclease in a host cell and thereby provide a cellular endonuclease activity in a sequence-specific manner in the host cell, and wherein cleavage of the functional nucleic acid by the endonuclease inactivates the cellular endonuclease activity.

The present disclosure provides a functional nucleic acid comprising: i) one or more coding nucleotide sequences encoding a sequence-specific endonuclease; ii) one or more regulatory sequences operably linked to the one or more coding nucleotide sequences; and iii) one or more endonuclease-recognized sequences, wherein the endonuclease-recognized sequences render the nucleic acid cleavable by the sequence-specific endonuclease in a cellular context, wherein the functional nucleic acid is configured to express the endonuclease in a host cell and thereby to provide in the host cell a sequence-specific cellular endonuclease activity, and wherein cleavage of the functional nucleic acid by the endonuclease inactivates the cellular endonuclease activity. The present disclosure provides a functional nucleic acid comprising: i) a nucleotide sequence encoding an RNA-guided site-specific endonuclease (e.g., a CRISPR/Cas endonuclease); and ii) target nucleotide sequences flanking the RNA-guided site-specific endonuclease-encoding nucleotide sequence, wherein target nucleotide sequences are cleavable by the RNA-guided site-specific endonuclease. In some cases, the functional nucleic acid comprises a first endonuclease-recognized sequence and a second endonuclease-recognized sequence flanking 5' and 3' sides of a first region of the functional nucleic acid, wherein the first region comprises at least one of the coding nucleotide sequences or at least one of the regulatory sequences. In some cases, the first region comprises all of the coding nucleotide sequences. In some cases, the genome-editing endonuclease comprises a clustered regularly interspaced short palindromic repeats (CRISPR) associated (Cas) endonuclease, a zinc finger nuclease (ZFN), or a transcription activator-like effector nuclease (TALEN®). In some cases, the genome-editing endonuclease is a CRISPR/Cas endonuclease. In some cases, the one or more coding nucleotide sequences comprises a nucleotide sequence encoding a Cas endonuclease and a corresponding guide RNA that hybridizes to a target nucleic acid in a sequence-specific manner in the host cell. In some cases, the guide RNA is a single guide RNA. In some cases, the one or more coding nucleotide sequences further comprises a nucleotide sequence encoding a CRISPR RNA (crRNA). In some cases, the functional nucleic acid comprises a first and second adeno-associated virus (AAV) inverted terminal repeats (ITRs) defining 5' and 3' ends, respectively, of a second region of the functional nucleic acid, wherein the second region comprises the one or more coding nucleotide sequences, the one or more regulatory sequences, and the one or more endonuclease-recognized sequences. In some cases, the regulatory sequences comprise a promoter and/or an enhancer. In some cases, each of the one or more endonuclease-recognized sequences comprise a nucleotide sequence having 5 nt or fewer mismatches, and/or at least 70% sequence identity to the target sequence for the sequence-specific endonuclease. In some cases, the target sequence has a length of 15 nt or more. In some cases, the target sequence comprises a genomic sequence of the host cell. In some cases, the target sequence comprises a unique genomic sequence. In some cases, the host cell is a mammalian cell, an algal cell, a yeast cell, a plant cell, an insect cell, an arthropod cell, a reptile cell, a bird cell, a fish cell, an amphibian cell, a protozoan parasite, or a helminth cell. In some cases, the host cell is a mammalian cell. In some cases, the mammalian cell is a human cell. The present disclosure provides an expression vector comprising a functional nucleic acid as described above or elsewhere herein. The present disclosure provides an isolated recombinant adeno-associated virus (rAAV) virion comprising: i) an AAV capsid protein; and ii) a functional nucleic acid as described above or elsewhere herein, or an expression vector as described above or elsewhere herein.

The present disclosure provides a method comprising: a) introducing a first heterologous nucleic acid into a host cell comprising a genomic nucleic acid, wherein the first heterologous nucleic acid comprises: i) one or more coding nucleotide sequences encoding a sequence-specific endonuclease; and ii) one or more endonuclease-recognized sequences, wherein the genomic nucleic acid comprises a target site comprising a predetermined target sequence for the endonuclease, the first heterologous nucleic acid is configured to express the endonuclease in the host cell and cleave the genomic nucleic acid at the target site, the endonuclease-recognized sequences render the functional nucleic acid cleavable by the endonuclease in a cellular context, and cleavage of the first heterologous nucleic acid by the endonuclease inactivates the cellular endonuclease activity. In some cases, the first heterologous nucleic acid comprises a functional nucleic acid as described above, or elsewhere herein wherein the target sequence comprises a unique genomic sequence, and wherein the host cell is a plant cell, a mammalian cell, an insect cell, an arthropod cell, a reptile cell, a protozoan, a helminth cell, a yeast cell, an algal cell, a fungal cell, or an amphibian cell. In some cases, the total number of copies of the endonuclease-recognized sequences is greater than the number of target sites in the host cell. In some cases, the introducing step (a) comprises contacting an rAAV virion comprising the first heterologous nucleic acid with the host cell. In some cases, the method further comprises: b) introducing a second heterologous nucleic acid into the host cell, wherein the second heterologous nucleic acid comprises a nucleotide sequence configured to promote homologous recombination with the genomic nucleic acid at the target site when the endonuclease cleaves the genomic nucleic acid in a sequence-specific manner. In some cases, introducing step (b) comprises contacting an rAAV virion comprising the second heterologous nucleic acid with the host cell. In some cases, the host cell is a mammalian cell. In some cases, the mammalian cell is a human cell. In some cases, the host cell is in vivo. In some cases, the host cell is in vitro. In some cases, the host cell is an ex vivo host cell.

The present disclosure provides a self-inactivating genome editing system, comprising: i) a functional nucleic acid as described above or elsewhere herein, or an expression vector as described above or elsewhere herein in a host cell comprising a genomic nucleic acid; and ii) a sequence-specific endonuclease in the host cell expressed from the functional nucleic acid or the expression vector, wherein the genomic nucleic acid comprises a target site comprising a target sequence for the endonuclease, and wherein the endonuclease provides a cellular endonuclease activity against the genomic nucleic acid in a first sequence-specific manner. In some cases, the system further comprises a second heterologous nucleic acid configured to recombine at the target site in a second sequence-specific manner when the endonuclease cleaves the genomic nucleic acid in the first sequence-specific manner.

The present disclosure provides a kit comprising: a) a functional nucleic acid as described above or elsewhere herein, or an expression vector as described above or elsewhere herein; and b) a packaging configured to contain the functional nucleic acid or the expression vector. In some cases, the kit further comprises a second heterologous nucleic acid configured to recombine at a genomic target site of a host cell in a sequence-specific manner when the endonuclease cleaves a genomic nucleic acid of the host cell at the genomic target site.

The present disclosure provides a self-inactivating genome editing system, comprising: a) a functional nucleic acid comprising: i) a nucleotide sequence encoding an RNA-guided site-specific endonuclease; and ii) target nucleotide sequences flanking the RNA-guided site-specific endonuclease-encoding nucleotide sequence, wherein target nucleotide sequences are cleavable by the RNA-guided site-specific endonuclease; and b) a guide RNA that comprises: i) a DNA-targeting segment comprising a nucleotide sequence that is complementary to a nucleotide sequence in a target DNA; and ii) a protein-binding segment that interacts with the RNA-guided site-specific endonuclease. In some cases, the RNA-guided site-specific endonuclease is a Cas9 polypeptide, and wherein the guide RNA is a Cas9 guide RNA. In some cases, the Cas9 guide RNA is a single-guide RNA.

DEFINITIONS

Figure 1:
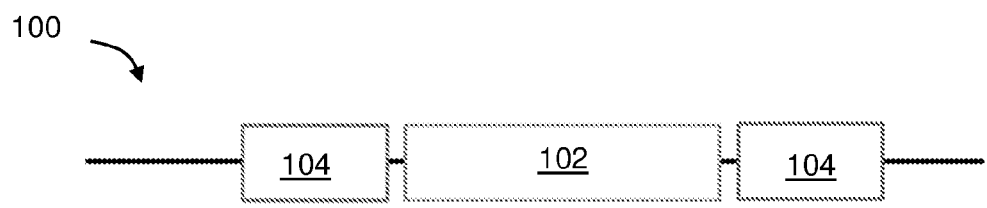
FIG. 1 is a schematic diagram showing a nucleic acid encoding a self-inactivating genome editing nuclease, according to embodiments of the present disclosure.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a DNA target nucleic acid base pairs with a guide RNA, etc.): guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a protein-binding segment (dsRNA duplex) of a guide RNA molecule; of a target nucleic acid base pairing with a guide RNA, etc.) is considered complementary to both a uracil (U) and to an adenine (A). For example, when a G/U base-pair can be made at a given nucleotide position of a protein-binding segment (e.g., dsRNA duplex) of a guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). Temperature, wash solution salt concentration, and other conditions may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a bulge, a loop structure or hairpin structure, etc.). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656), the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489), and the like.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a Cas9 protein/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_D$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_D$.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various convenient methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein (and therefore the DNA and the mRNA both encode the protein), or a DNA polynucleotide may encode an RNA that is not translated into protein (e.g. tRNA, rRNA, microRNA (miRNA), a "non-coding" RNA (ncRNA), a guide RNA, etc.).

"Coding sequence" as used herein, may refer to a nucleotide sequence that encodes a gene product, e.g., a non protein-encoding RNA or a protein gene product.

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," "regulatory sequence", and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide RNA) or a coding sequence (e.g., Cas9 polypeptide, or Cas9 polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

An "enhancer" as used herein may refer to a cis-acting regulatory element that acts on a promoter to increase transcription relative to the level of expression with the promoter alone. The regulatory element containing the promoter may include enhancer sequences as well (e.g., CMV or SV40).

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

"Heterologous," as used herein, means a moiety (e.g., a nucleic acid molecule, a portion of a nucleotide or polypeptide sequence, etc.) that is not found in an unmodified state. For example, a nucleic acid or protein that is heterologous to a host cell is different from nucleic acids or proteins found in the host cell that is not modified by introducing the nucleic acid or protein. The nucleic acid or protein may be different from those in an unmodified host cell based on sequence and/or structure. In a chimeric protein, e.g., a chimeric Cas9 protein, the RNA-binding domain of a naturally-occurring bacterial Cas9 polypeptide (or a variant thereof) may be fused to a heterologous polypeptide sequence (i.e. a polypeptide sequence from a protein other than Cas9 or a polypeptide sequence from another organism). The heterologous polypeptide sequence may exhibit an activity (e.g., enzymatic activity) that will also be exhibited by the chimeric Cas9 protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant Cas9 polypeptide, a variant Cas9 polypeptide may be fused to a heterologous polypeptide (i.e. a polypeptide other than Cas9), which exhibits an activity that will also be exhibited by the fusion variant Cas9 polypeptide. A heterologous nucleic acid sequence may be linked to a variant Cas9 polypeptide (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. An example of such a case is a DNA (a recombinant) encoding a wild-type protein where the DNA sequence is codon optimized for expression of the protein in a cell (e.g., a eukaryotic cell) in which the protein is not naturally found (e.g., expression of a CRISPR/Cas endonuclease in a eukaryotic cell). A codon-optimized DNA can therefore be recombinant and non-naturally occurring while the protein encoded by the DNA may have a wild type amino acid sequence.

Thus, the term "recombinant" polypeptide does not necessarily refer to a polypeptide whose amino acid sequence does not naturally occur. Instead, a "recombinant" polypeptide is encoded by a recombinant non-naturally occurring DNA sequence, but the amino acid sequence of the polypeptide can be naturally occurring ("wild type") or non-naturally occurring (e.g., a variant, a mutant, etc.). Thus, a "recombinant" polypeptide is the result of human intervention, but may have a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence (or the coding sequence can also be said to be operably linked to the promoter) if the promoter affects its transcription or expression. There may be intervening residues between the promoter and coding region so long as this functional relationship is maintained.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, diethylaminoethyl (DEAE)-dextran mediated transfection, liposome-mediated transfection, particle gun technology, calcium phosphate precipitation, direct micro injection, nanoparticle-mediated nucleic acid delivery (see, e.g., Panyam et. al Adv Drug Deliv Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.). A "sequence-specific endonuclease" cleaves a nucleic acid that contains one or more contiguous sequences of nucleotides with a specific identity and order of nucleotides at a specific position relative to the contiguous sequences, under conditions in which cleavage of the nucleic acid at other positions in the nucleic acid, or of a nucleic acid that does not contain such contiguous sequences is substantially absent. In some cases, the functional endonuclease may include two or more gene products (e.g., two or more proteins, a combination of protein and RNA, etc.) that together provide for sequence-specificity and/or catalytic activity.

A "genome editing endonuclease" is an endonuclease, e.g., sequence-specific endonuclease, which can be used for the editing of a cell's genome (e.g., by cleaving at a targeted location within the cell's genomic DNA). Examples of genome editing endonucleases include but are not limited to: (i) Zinc finger nucleases, (ii) TAL endonucleases, and (iii) CRISPR/Cas endonucleases. Examples of CRISPR/Cas endonucleases include class 2 CRISPR/Cas endonucleases such as: (a) type II CRISPR/Cas proteins, e.g., a Cas9 protein; (b) type V CRISPR/Cas proteins, e.g., a Cpf1 polypeptide, a C2c1 polypeptide, a C2c3 polypeptide, and the like; and (c) type VI CRISPR/Cas proteins, e.g., a C2c2 polypeptide.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. In some embodiments, a complex comprising a CRISPR/Cas protein (e.g., a Cas9 protein) and a corresponding guide RNA is used for targeted cleavage of a double stranded DNA (dsDNA), e.g., induction of a double-stranded DNA break (DSB).

A "target sequence" as used herein, may refer to a nucleotide sequence that a sequence-specific endonuclease, e.g., a genome-editing endonuclease, is specifically designed to bind (e.g., by providing Cas9 with a guide RNA having a sequence that is complementary to the target sequence). In some cases, the nucleic acid containing the sequence is optimally cleaved by the sequence-specific endonuclease, e.g., genome-editing endonuclease, specifically designed to bind the sequence. The target sequence may be defined by the identity and order of a single contiguous stretch of nucleotides in the nucleic acid, or may be defined by the identity and order of two or more sets of a contiguous stretch of nucleotides, where intervening nucleotide sequences (e.g., a spacer) may separate the different sets. The spacer may contain any sequence of nucleotides. The size of the spacer may depend on the particular sequence-specific endonuclease (e.g., genome-editing endonuclease) that is used. The cleavage of the nucleic acid may occur at a site specifically predetermined relative to the position of the target sequence, depending on the sequence-specific endonuclease, e.g., genome-editing endonuclease.

"Endonuclease-recognized sequence", as used herein, may refer to a nucleotide sequence that can be bound by a sequence-specific endonuclease, e.g., a genome editing endonuclease, where the presence of the sequence in a nucleic acid renders the nucleic acid cleavable by the endonuclease in a cellular context (i.e., the sequence-specific endonuclease, e.g., genome-editing endonuclease, can cleave the nucleic acid containing the nucleotide sequence at a specific position relative to the nucleotide sequence while leaving other sites in the nucleic acid, or other nucleic acids that do not contain the nucleotide sequence substantially uncleaved). The sequence may be identical to the target nucleotide sequence for the sequence-specific endonuclease, e.g., genome-editing endonuclease, or may include one or more mismatches compared to the target nucleotide sequence.

A "target nucleic acid" as used herein is a polynucleotide (e.g., DNA such as genomic DNA) that includes a site ("target site" "target sequence" or "endonuclease-recognized sequence") targeted by a sequence-specific endonuclease, e.g., genome-editing endonuclease. When the sequence-specific endonuclease, e.g., genome editing endonuclease, is a CRISPR/Cas endonuclease, the target sequence is the sequence to which the guide sequence of a subject CRISPR/Cas guide RNA (e.g., a Cas9 guide RNA) will hybridize. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. For a double stranded target nucleic acid, the strand of the target nucleic acid that is complementary to and hybridizes with the guide RNA is referred to as the "complementary strand" or "target strand"; while the strand of the target nucleic acid that is complementary to the "target strand" (and is therefore not complementary to the guide RNA) is referred to as the "non-target strand" or "non-complementary strand".

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a subject genome targeting composition, and include the progeny of the original cell (e.g., when the cell has been transformed by the nucleic acid, or when the cells genome has been modified by the genome targeting composition). It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a subject genome targeting composition, e.g., which can include a nucleic acid, e.g., an expression vector. For example, a subject bacterial host cell can be a genetically modified bacterial host cell by virtue of introduction into a suitable bacterial host cell of an exogenous nucleic acid (e.g., a plasmid or recombinant expression vector) and a subject eukaryotic host cell can be a genetically modified eukaryotic host cell (e.g., a mammalian cell, an algal cell, a yeast cell, a plant cell, an insect cell, an arthropod cell, a reptile cell, an amphibian cell, a protozoan parasite, or a helminth cell), by virtue of introduction into a suitable eukaryotic host cell of an exogenous nucleic acid.

"Inactivate", as used herein, may refer to reducing or substantially abolishing functional activity of enzymatic activity, e.g., nuclease activity. The enzymatic activity may be reduced or abolished by reducing or abolishing expression of the enzyme, e.g., nuclease, from a nucleic acid that is configured to express the enzyme, e.g., nuclease.

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" or "rAAV virion" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV virion". Thus, production of rAAV virion necessarily includes production of an rAAV vector, as such a vector is contained within an rAAV virion.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

"Recombine" as used herein, may refer to a sequence homology-dependent exchange of a piece of a first nucleic acid flanked by flanking sequences, with a piece of a second nucleic acid flanked by sequences homologous to the flanking sequences of the first nucleic acid.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present disclosure is further described, it is to be understood that the disclosed subject matter is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a nucleic acid" includes a plurality of such nucleic acids and reference to "the nuclease" includes reference to one or more nucleases and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the disclosed subject matter, which are, for clarity, described in the context of separate embodiments, may also be provided in combination in a single embodiment. Conversely, various features of the disclosed subject matter, which are, for brevity, described in the context of a single embodiment, may also be provided separately or in any suitable sub-combination. All combinations of the embodiments pertaining to the disclosure are specifically embraced by the disclosed subject matter and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the disclosed subject matter is not entitled to antedate such publication by virtue of prior invention. Further, the dates of publication provided may be different from the actual publication dates which may need to be independently confirmed.

DETAILED DESCRIPTION

As summarized above, the present disclosure includes a functional nucleic acid encoding a sequence-specific endonuclease, where the nucleic acid also includes an endonuclease-recognized nucleotide sequence that renders the functional nucleic acid cleavable by the sequence-specific endonuclease when the endonuclease is expressed in a host cell. The endonuclease-recognized nucleotide sequence is positioned in the functional nucleic acid such that when the functional nucleic acid is cleaved by a sequence-specific endonuclease encoded by a functional nucleic acid of the present disclosure, further expression of the endonuclease from the cleaved functional nucleic acid is abolished. Thus, expression of the sequence-specific endonuclease in the host cell is reduced as more sequence-specific endonuclease accumulates in the host cell and cleaves the functional nucleic acids, which may cause, e.g., excision of pieces of the functional nucleic acid that are flanked by endonuclease-recognized nucleotide sequences. Such a self-inactivating endonuclease-expression system may provide for a transient, sequence-specific endonuclease activity (e.g., genome editing activity) in the host cell, where the transient endonuclease activity is sufficient to cleave a target nucleic acid of the host cell (i.e., a target nucleic acid other than the nucleic acid from which the endonuclease is expressed, such as genomic DNA), but does not lead to accumulation of the sequence-specific endonuclease in the host cell. As a result, cleavage by the nuclease at off-target sites in the host nucleic acid, as well as any in vivo inflammatory responses from overexpression of the endonuclease, may be reduced or prevented.

In some cases, the sequence-specific endonuclease is a genome editing endonuclease, which can be programmed to bind and cleave genomic DNA sequences in a host cell in which the present functional nucleic acid expresses the sequence-specific endonuclease.

Further aspects of the present disclosure are now described.

Functional Nucleic Acids

A functional nucleic acid of the present disclosure (also referred to as a "self-inactivating endonuclease-encoding nucleic acid" or a "self-inactivating site-specific endonuclease-encoding nucleic acid") comprises a nucleotide sequence that encodes an endonuclease, e.g., a site-specific endonuclease, e.g., an RNA-guided endonuclease. A functional nucleic acid of the present disclosure may be described with reference to the Figures. With reference to FIG. 1, an embodiment of the present functional nucleic acid (e.g., DNA) 100 may include a coding sequence 102 encoding a sequence-specific endonuclease, and one or more endonuclease-recognized sequences 104, which are sequences that the sequence-specific endonuclease, when expressed, can bind to and that direct cleavage of the functional nucleic acid by the sequence-specific endonuclease. The sequence-specific endonuclease may include one or more components (e.g., a Cas9 protein and gRNA; an engineered Zinc finger protein pair, etc.) and the coding sequence may encode some or all of the components of the sequence-specific endonuclease. The sequence-specific endonuclease may be any suitable endonuclease, as described below. The functional nucleic acid is configured to express the sequence-specific endonuclease, and thus may include any suitable regulatory sequences operably linked to the coding sequence.

Figure 2A:
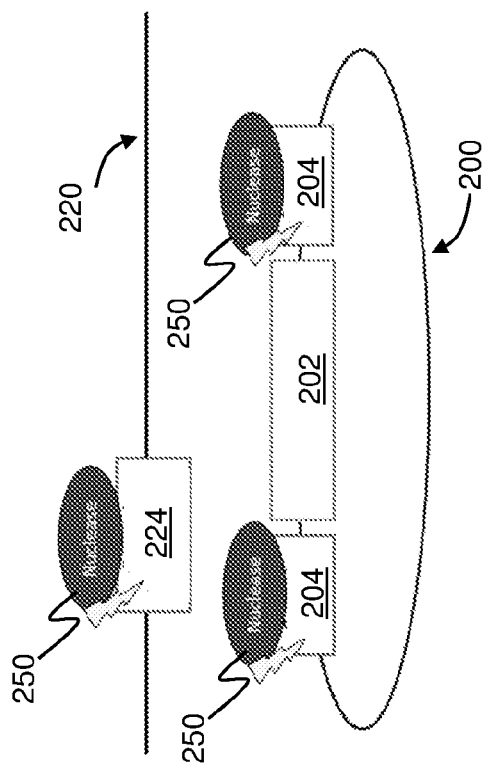
FIGS. 2A-2C are a collection of schematic diagrams illustrating self-inactivation of a genome editing nuclease, according to embodiments of the present disclosure.
Figure 2B:
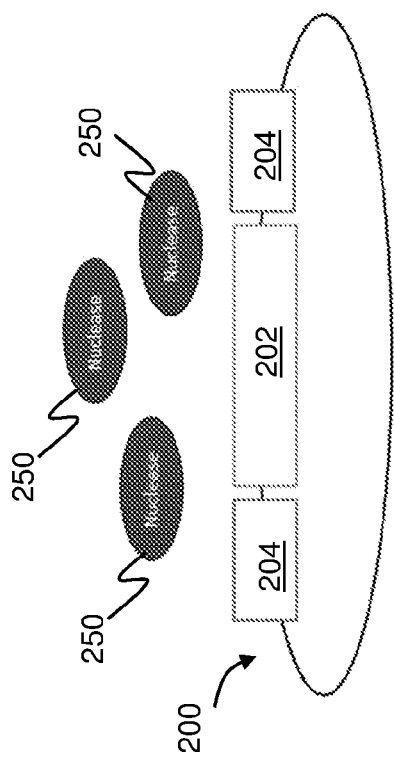
Figure 2C:
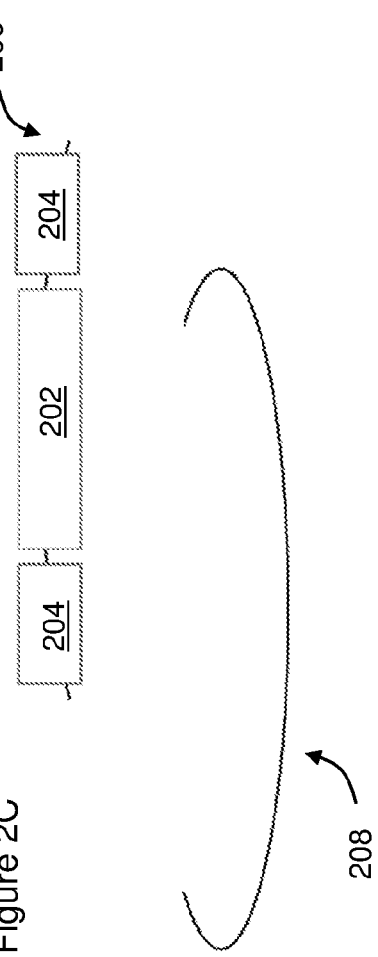

FIGS. 2A-2C depicts an embodiment of the present disclosure, where a functional nucleic acid 200 expresses sequence-specific endonucleases 250 (FIG. 2A) when introduced into a suitable environment, e.g., a host cell. The sequence-specific endonucleases may be engineered to direct the nuclease activity to a target site 224 in a host nucleic acid 220, where the target site may include a target sequence for the sequence-specific endonucleases (FIG. 2B). The host nucleic acid may then be cleaved at a predetermined position relative to the binding site, i.e., target sequence. In some cases, the sequence-specific endonuclease is a genome editing nuclease and the host nucleic acid is genomic DNA of the host cell. The sequence-specific endonucleases also can bind to and cleave the functional nucleic acid, by binding to the endonuclease-recognized sequences 204. Cleavage of the functional nucleic acid (FIG. 2C) by the sequence-specific endonucleases may abolish expression of the sequence-specific endonucleases encoded by the coding sequence 202 of the functional nucleic acid, e.g., by excision of the coding portion 206 of the functional nucleic acid containing the coding sequence from the remaining portion 208, which may contain the regulatory sequences, or any other functional sequences required for expression of sequence-specific endonuclease activity in the host cell.

The endonuclease-recognized sequences may be any suitable nucleotide sequence that is configured to induce cleavage of the functional nucleic acid at a specific site relative to the position of the endonuclease-recognized sequence, and to provide self-inactivation of the sequence-specific nuclease activity (e.g., sequence-specific nuclease expression) in a host cell of interest. In some cases, the endonuclease-recognized sequence includes a nucleotide sequence having 5 nt or fewer, e.g., 4 nt or fewer, 3 nt or fewer, 2 nt or fewer, including 1 nt or fewer, or a nucleotide sequence with no mismatches, with the target sequence for the sequence-specific endonuclease. In some embodiments, the endonuclease-recognized sequence includes a nucleotide sequence having at least 70%, e.g., at least 80%, at least 85%, at least 90%, at least 95%, at least 97%, at least 99%, and up to 100% sequence identity to the target sequence for the sequence-specific endonuclease. In some cases, the endonuclease-recognized sequence is the target sequence of the sequence-specific nuclease.

The functional nucleic acid may include any suitable number of the present endonuclease-recognized sequences that achieves self-inactivation in a host cell, as described herein. In some embodiments, the functional nucleic acid includes one or more, e.g., 2 or more, 3 or more, 4 or more, 5 or more, including 6 or more endonuclease-recognized sequences, and in some cases, includes 10 or fewer, e.g., 9 or fewer, 8 or fewer, 7 or fewer, 6 or fewer, 5 or fewer, including 4 or fewer endonuclease-recognized sequences. In some cases, the functional nucleic acid includes 1 to 10, e.g., 1 to 8, 1 to 6, 1 to 4, including 2 to 4 endonuclease-recognized sequences.

The endonuclease-recognized sequences may be positioned relative to the coding sequences and regulatory sequences of the functional nucleic acid in any suitable manner that achieves self-inactivation in a host cell, as described herein. In some cases, the endonuclease-recognized sequences flank the coding sequence(s) (as shown, e.g., in FIG. 1A) and/or regulatory sequence(s) on both 5' and 3' sides, such that the flanked sequence(s) is excised from the rest of the functional nucleic acid upon cleavage by the sequence-specific endonuclease directed by both flanking endonuclease-recognized sequences. Thus, in some cases, the present functional nucleic acid may include a nucleotide sequence represented by the formula: 5'-X-Y"-X-3', where Y" are n coding sequences that encode a sequence-specific endonuclease, where n is an integer of 1 or greater, e.g., 2 or greater, including 3 or greater; and X is an endonuclease-recognized sequence. The nucleotide-recognized sequence at one flanking end of the coding sequence in some cases may be the reverse complement of the other flanking end. Thus, in some cases, the present functional nucleic acid may include a nucleotide sequence represented by the formula: 5'-X-Y"-X'-3', where Y" are n coding sequences that encode a sequence-specific endonuclease, where n is an integer of 1 or greater, e.g., 2 or greater, including 3 or greater; X is an endonuclease-recognized sequence; and X' is the reverse complement of X.

The flanking endonuclease-recognized sequences may define the 5' and 3' ends of the coding and/or regulatory sequences, or may include a suitable spacer sequence between the 5' and/or 3' ends and the respective endonuclease-recognized sequences. Thus, in some cases, the present functional nucleic acid may include a nucleotide sequence represented by the formula: 5'-X-S-Y"-S-X-3' or 5'-X-S-Y"-S-X'-3', where Y" are n coding sequences that encode a sequence-specific endonuclease, where n is an integer of 1 or greater, e.g., 2 or greater, including 3 or greater; X is an endonuclease-recognized sequence; X' is the reverse complement of X; and S is a spacer sequence. The spacer sequence may by any suitable sequence of any suitable length (e.g., 1 nt or more, e.g., 2 nt or more, 3 nt or more, 4 nt or more, 5 nt or more, 6 nt or more, 8 nt or more, 10 nt or more, including 20 nt or more in length).

In some embodiments, where the sequence-specific endonuclease includes two or more components encoded by multiple coding sequences (e.g., Cas9 and gRNA; engineered ZFN pair or TALEN® pair, etc.), the endonuclease-recognized sequences flank at least some, e.g., at least one, at least two, at least three, or all, of the multiple coding sequences encoding the sequence-specific endonucleases. Thus, in some cases, the present functional nucleic acid may include a nucleotide sequence represented by the formula: 5'-X-Y''-X-Y'''-3' or 5'-X-Y''-X'-Y'''-3', where Y'' and Y''' are n and m coding sequences, respectively, that collectively encode a sequence-specific endonuclease, where n and m are each an integer of 1 or greater, e.g., 2 or greater, including 3 or greater; X is an endonuclease-recognized sequence; and X' is the reverse complement of X.

In some cases, the endonuclease-recognized sequences define the 5' and 3' ends of at least part of the coding sequence(s) and/or regulatory sequence(s). Thus, in some embodiments, the present functional nucleic acid may include a nucleotide sequence represented by the formula: 5'-P-X-Y''-X-3' or 5'-P-X-Y''-X'-3', where Y'' are n coding sequences that encode a sequence-specific endonuclease, where n is an integer of 1 or greater, e.g., 2 or greater, including 3 or greater; P is a regulatory sequence operably coupled to the coding sequence(s); X is an endonuclease-recognized sequence; and X' is the reverse complement of X.

In some cases, the endonuclease-recognized sequences flank a regulatory sequence, e.g., promoter, such that the regulatory sequence will be excised when cleaved by the sequence-specific endonuclease, thereby preventing further expression of the sequence-specific endonuclease from the cleaved functional nucleic acid. Thus, in some embodiments, the present functional nucleic acid may include a nucleotide sequence represented by the formula: 5'-X-P-X-Y''-3' or 5'-X-P-X'-Y''-3', where Y'' are n coding sequences that encode a sequence-specific endonuclease, where n is an integer of 1 or greater, e.g., 2 or greater, including 3 or greater; P is a regulatory sequence operably coupled to the coding sequence(s); X is an endonuclease-recognized sequence; and X' is the reverse complement of X.

In some embodiments, an endonuclease-recognized sequence is included in an intervening sequence, e.g., intron, within a coding sequence. Thus, in some embodiments, the present functional nucleic acid may include a nucleotide sequence represented by the formula: 5'-X-Y'-I(X)-Y''-3' or 5'-X-Y'-I(X')-Y''-3' or 5'-Y'-I(X)-Y''-X-3' or 5'-Y'-I(X)-Y''-X'-3', where Y' and Y'' are exons of a coding sequence that encode a sequence-specific endonuclease; I is an intronic sequence that includes a endonuclease-recognized sequence; X is an endonuclease-recognized sequence; and X' is the reverse complement of X.

Any other suitable combinations and order of coding sequence, regulatory sequences, spacers, and/or intervening sequences, etc., are also included in the present disclosure.

The functional nucleic acid may include any other suitable sequence elements that facilitate the delivery, expression, and/or inactivation of the sequence-specific endonuclease in a host cell. Suitable sequence elements include, without limitation, regulatory sequences and viral delivery elements. Regulatory sequences may be operably linked to the coding sequences of the present functional nucleic acid. Suitable regulator sequences may include promoters and/or enhancers for driving expression, that is, transcriptional activation, of the nucleic acid of interest. Promoters of interest include, without limitation, ubiquitously acting promoters, for example, the CMV-β-actin promoter, the EF-1 alpha promoter, and the like; tissue-specific promoter that are active selectively or preferentially in particular cell populations over other cell populations; or inducible promoters that respond to the presence of drugs, such as tetracycline. Other examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a Rous sarcoma virus (RSV) promoter, synthetic promoters, hybrid promoters, and the like. By transcriptional activation, it is intended that transcription will be increased above basal levels in the host cell by at least about 10 fold, by at least about 100 fold, more usually by at least about 1000 fold.

In some cases, the functional nucleic acid includes viral delivery elements that facilitate delivery of the functional nucleic acid into a host cell by viral transduction. The viral delivery elements may be any suitable sequence of nucleotides that promote delivery of the functional nucleic acid into a host cell by viral transduction. Suitable viral delivery elements include, without limitation, long terminal repeats (LTRs), such as adeno-associated virus (AAV) inverted terminal repeats (ITRs), and retrovirus (e.g., lentivirus, gamma-retrovirus, etc.) long terminal repeats (LTRs).

Sequence-Specific Endonucleases

The coding sequence of the present functional nucleic acid may encode any suitable endonuclease that can be engineered to cleave a nucleic acid (e.g., cause a double-stranded break (DSB) in the nucleic acid backbones) in a target sequence-specific manner, at a specific site relative to the position of the target sequence. Thus, the specificity for the sequence-specific endonuclease to bind and cleave a nucleic acid may be defined by a target sequence of interest. In some cases, the target sequence includes a genomic sequence of the host cell. The genomic sequence may be a DNA sequence of the eukaryotic host cell nucleus, mitochondrion, choloroplast, etc. In some cases, the genomic sequence may be a DNA sequence of a mammal, a human, a mouse, a rat, a non-human primate, a bird, an insect, an arthropod, a reptile, an amphibian, a plant, an algae, etc. In some cases, the target sequence includes a genomic sequence that is unique (i.e., the target sequence occurs at one locus within the genomic sequence, where the actual number of the target sequence may be one for a haploid host cell, or for a diploid host cell that is heterozygous at the target sequence genomic locus; or two for a diploid host cell that is homozygous at the target sequence genomic locus, and so on).

The target sequence of the sequence-specific endonuclease may have any suitable length (excluding any spacer sequences) to achieve sequence-specific targeting of the endonuclease. In some embodiments, the target sequence is 15 nt or longer, e.g., 16 nt or longer, 17 nt or longer, 18 nt or longer, 19 nt or longer, 20 nt or longer, 21 nt or longer, 22 nt or longer, 23 nt or longer, 24 nt or longer, 25 nt or longer, 26 nt or longer, 27 nt or longer, 28 nt or longer, 30 nt or longer, 35 nt or longer, including 40 nt or longer, and in some embodiments, is 100 nt or shorter, e.g., 90 nt or shorter, 80 nt or shorter, 70 nt or shorter, 60 nt or shorter, 50 nt or shorter, 40 nt or shorter, 35 nt or shorter, including 30 nt or shorter. In some cases, the target sequence is in the range of 15 to 100 nt, e.g., 16 to 90 nt, 17 to 80 nt, 18 to 60 nt, 18 to 50 nt, 18 to 40 nt, 18 to 35 nt, including 18 to 30 nt long.

Where the target sequence is defined by two or more contiguous regions of specific nucleotide sequences, a spacer dividing the contiguous regions may have any suitable length, depending on the sequence-specific endonuclease used (i.e., encoded by the coding sequence). In some cases, the spacer has a length of 5 nt or more, e.g., 6 nt or more, 7 nt or more, 8 nt or more, 10 nt or more, 12 nt or more, including 15 nt or more, and in some embodiments, a length of 30 nt or less, e.g., 25 nt or less, 20 nt or less, 18 nt or less, including 16 nt or less. In some cases, the spacer has a length in the range of 5 to 30 nt, e.g., 6 to 25 nt, 6 to 20 nt, including 6 to 18 nt.

A sequence-specific endonuclease encoded by the coding sequence(s) may include endonucleases that are formed by one or more, e.g., two or more, 3 or more, such as 4 or more, components. In some cases, the endonuclease includes multiple components (e.g., engineered ZFN pair, Cas9/gRNA, gRNA-programmed Cas9 pair, TALEN® pair). In some cases, the endonuclease includes one or more protein components and one or more non-protein components (e.g., nucleic acid components, such as gRNA and CRISPR RNA (crRNA)).

Examples of suitable sequence-specific, e.g., genome editing, endonucleases include but are not limited to zinc finger nucleases, meganucleases, TAL-effector DNA binding domain-nuclease fusion proteins (transcription activator-like effector nucleases (TALEN®s)), and CRISPR/Cas endonucleases (e.g., class 2 CRISPR/Cas endonucleases such as a type II, type V, or type VI CRISPR/Cas endonucleases). Thus, in some embodiments, a coding sequence of the present functional nucleic acid can encode for one or more sequence-specific, e.g., genome editing, endonucleases selected from: a zinc finger nuclease, a TAL-effector DNA binding domain-nuclease fusion protein (TALEN), and a CRISPR/Cas endonuclease (e.g., a class 2 CRISPR/Cas endonuclease such as a type II, type V, or type VI CRISPR/Cas endonuclease). In some cases, a sequence-specific endonuclease includes a zinc finger nuclease or a TALEN. In some cases, a sequence-specific endonuclease includes a class 2 CRISPR/Cas endonuclease. In some cases, a sequence-specific endonuclease includes a class 2 type II CRISPR/Cas endonuclease (e.g., a Cas9 protein). In some cases, a sequence-specific endonuclease includes a class 2 type V CRISPR/Cas endonuclease (e.g., a Cpf1 protein, a C2c1 protein, or a C2c3 protein). In some cases, a sequence-specific endonuclease includes a class 2 type VI CRISPR/Cas endonuclease (e.g., a C2c2 protein).

As described in more detail below, a CRISPR/Cas endonuclease interacts with (binds to) a corresponding guide RNA to form a ribonucleoprotein (RNP) complex that is targeted to a particular site in a target nucleic acid, e.g., a target genome, via base pairing between the guide RNA and a target sequence within the target nucleic acid, e.g., a target genome. A guide RNA includes a nucleotide sequence (a guide sequence) that is complementary to a sequence (the target site) of a target nucleic acid. Thus, when a functional nucleic acid includes a coding sequence encoding a CRISPR/Cas endonuclease (e.g., a class 2 CRISPR/Cas endonuclease), it may also include a corresponding guide RNA when being used in a method to cleave a target DNA. However, because the guide RNA can be readily modified in order to target any desired sequence within a target genome, in some cases, a functional nucleic acid includes a coding sequence encoding the CRISPR/Cas endonuclease but not the gRNA, and the desired corresponding guide RNA (or a nucleic acid encoding the corresponding guide RNA) is provided separately by a user.

In some cases, a sequence-specific, e.g., genome editing, endonuclease is a fusion protein that is fused to a heterologous polypeptide (also referred to as a "fusion partner"). In some cases, a sequence-specific, e.g., genome editing, nuclease is fused to an amino acid sequence (a fusion partner) that provides for subcellular localization, i.e., the fusion partner is a subcellular localization sequence (e.g., one or more nuclear localization signals (NLSs) for targeting to the nucleus, two or more NLSs, three or more NLSs, etc.). In some embodiments, a sequence-specific, e.g., genome editing, nuclease is fused to an amino acid sequence (a fusion partner) that provides a tag (i.e., the fusion partner is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the fusion partner can provide for increased or decreased stability (i.e., the fusion partner can be a stability control peptide, e.g., a degron, which in some cases is controllable (e.g., a temperature sensitive or drug controllable degron sequence).

Zinc Finger Nucleases (ZFNs)

In some embodiments, a coding sequence(s) of the present functional nucleic acid encodes a zinc-finger nuclease (ZFN). ZFNs are engineered double-strand break inducing proteins comprised of a zinc finger DNA binding domain and a double strand break inducing agent domain Engineered ZFNs consist of two zinc finger arrays (ZFAs), each of which is fused to a single subunit of a non-specific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two FokI nuclease monomers, ZFNs generate a functional site-specific endonuclease that creates a double-stranded break (DSB) in DNA at the targeted locus.

Useful zinc-finger nucleases include those that are known and those that are engineered to have specificity for one or more desired target sites (TS). Zinc finger domains are amenable for designing polypeptides which specifically bind a selected polynucleotide recognition sequence, for example, within the target site of the host cell genome. ZFNs consist of an engineered DNA-binding zinc finger domain linked to a non-specific endonuclease domain, for example nuclease domain from a Type IIs endonuclease such as HO or FokI. Alternatively, engineered zinc finger DNA binding domains can be fused to other double-strand break inducing agents or derivatives thereof that retain DNA nicking/cleaving activity. For example, this type of fusion can be used to direct the double-strand break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) J Biol Chem 276:29466-78; Dreier, et al., (2000) J Mol Biol 303:489-502; Liu, et al., (2002) J Biol Chem 277:3850-6), as well as those that recognize various CNN or TNN triplets (Dreier, et al., (2005) J Biol Chem 280:35588-97; Jamieson, et al., (2003) Nature Rev Drug Discov 2:361-8). See also, Durai, et al., (2005) Nucleic Acids Res 33:5978-90; Segal, (2002) Methods 26:76-83; Porteus and Carroll, (2005) Nat Biotechnol 23:967-73; Pabo, et al., (2001) Ann Rev Biochem 70:313-40; Wolfe, et al., (2000) Ann Rev Biophys Biomol Struct 29:183-212; Segal and Barbas, (2001) Curr Opin Biotechnol 12:632-7; Segal, et al., (2003) Biochemistry 42:2137-48; Beerli and Barbas, (2002) Nat Biotechnol 20:135-41; Carroll, et al., (2006) Nature Protocols 1:1329; Ordiz, et al., (2002) Proc Natl Acad Sci USA 99:13290-5; Guan, et al., (2002) Proc Natl Acad Sci USA 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809; WO05/014791; WO05/084190; WO08/021207; WO09/042186; WO09/054985; and WO10/065123.

If the sequence-specific, e.g., genome editing, endonuclease to be utilized is a zinc finger nuclease, optimal target sites may be selected using a number of publicly available online resources. See, e.g., Reyon et al., BMC Genomics 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a pre-constructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *Saccharomyces cerevisiae, Chlamydomonas reinhardtii, Arabidopsis thaliana, Drosophila melanogaster, Danio rerio, Caenorhabditis elegans*, and *Homo sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) can also be used. ZFNGenome provides information about each potential ZFN target site, including its chromosomal location and position relative to transcription initiation site(s). Users can query ZFNGenome using several different criteria (e.g., gene ID, transcript ID, target site sequence).

For more information on ZFNs, refer to U.S. Pat. No. 8,685,737, which is hereby incorporated by reference in its entirety.

TALENs

In some embodiments, a coding sequence(s) of the present functional nucleic acid encodes a TAL-effector DNA binding domain-nuclease fusion protein (TALEN®). A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain can be engineered to bind to a desired target sequence, and fused to a nuclease domain, e.g., from a type II restriction endonuclease, typically a nonspecific cleavage domain from a type II restriction endonuclease such as FokI (see e.g., Kim et al. (1996) Proc. Natl. Acad. Sci. USA 93:1156-1160). Other useful endonucleases may include, for example, HhaI, HindIII, Nod, BbvCI, EcoRI, BglI, and AlwI. Thus, in some embodiments, a TALEN® includes a TAL effector domain containing a plurality of TAL effector repeat sequences that, in combination, bind to a specific nucleotide sequence in the target DNA sequence, such that the TALEN® cleaves the target DNA within or adjacent to the specific nucleotide sequence. Suitable TALEN® includes those described in WO10/079430 and U.S. Patent Application Publication No. 2011/0145940.

In some embodiments, the TAL effector domain that binds to a specific nucleotide sequence within a target DNA that includes 10 or more DNA binding repeats, and in some cases 15 or more DNA binding repeats. In some embodiments, each DNA binding repeat includes a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

If the sequence-specific, e.g., genome editing, endonuclease to be utilized is a TALEN®, in some embodiments, optimal target sites may be selected in accordance with the methods described by Sanjana et al., Nature Protocols, 7:171-192 (2012), which is hereby incorporated by reference in its entirety. In brief, TALENs function as dimers, and a pair of TALEN®, referred to as the left and right TALEN®, target sequences on opposite strands of DNA. TALEN® can be engineered as a fusion of the TALE DNA-binding domain and a monomeric FokI catalytic domain. To facilitate FokI dimerization, the left and right TALEN® target sites can be chosen with a spacing of approximately 14-20 bases. Therefore, for a pair of TALEN®, each targeting 20-bp sequences, an optimal target site can have the form 5'-TN$^{19}$N$^{14-20}$N$^{19}$A-3', where the left TALEN targets 5'-TN$^{19}$-3' and the right TALEN targets the antisense strand of 5'-N$^{19}$A-3' (N=A, G, T or C).

For more information on TALENs, refer to U.S. Pat. No. 8,685,737, which is hereby incorporated by reference in its entirety.

Class 2 CRISPR/Cas Endonucleases

RNA-mediated adaptive immune systems in bacteria and archaea rely on Clustered Regularly Interspaced Short Palindromic Repeat (CRISPR) genomic loci and CRISPR-associated (Cas) proteins that function together to provide protection from invading viruses and plasmids. In some embodiments, a sequence-specific, e.g., genome editing, nuclease encoded by a coding sequence(s) of a functional nucleic acid of the present disclosure is a class 2 CRISPR/Cas endonuclease. In class 2 CRISPR systems, the functions of the effector complex (e.g., the cleavage of target DNA) are carried out by a single endonuclease (e.g., see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97). As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex.

Type II CRISPR/Cas Endonucleases (e.g., Cas 9)

In natural Type II CRISPR/Cas systems, Cas9 functions as an RNA-guided endonuclease that uses a dual-guide RNA having a crRNA and trans-activating crRNA (tracrRNA) for target recognition and cleavage by a mechanism involving two nuclease active sites in Cas9 that together generate double-stranded DNA breaks (DSBs), or can individually generate single-stranded DNA breaks (SSBs). The Type II CRISPR endonuclease Cas9 and engineered dual-(dgRNA) or single guide RNA (sgRNA) form a ribonucleoprotein (RNP) complex that can be targeted to a desired DNA sequence. Guided by a dual-RNA complex or a chimeric single-guide RNA, Cas9 generates site-specific DSBs or SSBs within double-stranded DNA (dsDNA) target nucleic acids, which are repaired either by non-homologous end joining (NHEJ) or homology-directed recombination (HDR).

As noted above, in some cases, a sequence-specific endonuclease of the present disclosure includes a type II CRISPR/Cas endonuclease. A type II CRISPR/Cas endonuclease is a type of class 2 CRISPR/Cas endonuclease. In some cases, the type II CRISPR/Cas endonuclease is a Cas9 protein. A Cas9 protein forms a complex with a Cas9 guide RNA. The guide RNA provides target specificity to a Cas9-guide RNA complex by having a nucleotide sequence (a guide sequence) that is complementary to a sequence (the target site) of a target nucleic acid (as described elsewhere herein). The Cas9 protein of the complex provides the site-specific activity. In other words, the Cas9 protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the Cas9 guide RNA.

A Cas9 protein can bind and/or modify (e.g., cleave, nick, methylate, demethylate, etc.) a target nucleic acid and/or a polypeptide associated with target nucleic acid (e.g., methylation or acetylation of a histone tail)(e.g., when the Cas9 protein includes a fusion partner with an activity). In some cases, the Cas9 protein is a naturally-occurring protein (e.g., naturally occurs in bacterial and/or archaeal cells). In other cases, the Cas9 protein is not a naturally-occurring polypeptide (e.g., the Cas9 protein is a variant Cas9 protein, a chimeric protein, and the like).

Examples of suitable Cas9 proteins include, but are not limited to, those set forth in SEQ ID NOs: 5-263, and 265-816. Naturally occurring Cas9 proteins bind a Cas9 guide RNA, are thereby directed to a specific sequence within a target nucleic acid (a target site), and cleave the target nucleic acid (e.g., cleave dsDNA to generate a double strand break, cleave ssDNA, cleave ssRNA, etc.). A chimeric Cas9 protein is a fusion protein including a Cas9 polypeptide that is fused to a heterologous protein (referred to as a fusion partner), where the heterologous protein provides an activity (e.g., one that is not provided by the Cas9 protein). The fusion partner can provide an activity, e.g., enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc.). In some cases a portion of the Cas9 protein (e.g., the RuvC domain and/or the HNH domain) exhibits reduced nuclease activity relative to the corresponding portion of a wild type Cas9 protein (e.g., in some cases the Cas9 protein is a nickase). In some cases, the Cas9 protein has reduced enzymatic activity relative to a wild-type Cas9 protein (e.g., relative to *Streptococcus pyogenes* Cas9).

Assays to determine whether a given protein interacts with a Cas9 guide RNA can be any convenient binding assay that tests for binding between a protein and a nucleic acid. Suitable binding assays (e.g., gel shift assays) will be known to one of ordinary skill in the art (e.g., assays that include adding a Cas9 guide RNA and a protein to a target nucleic acid).

Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art and can include adding a Cas9 guide RNA and a protein to a target nucleic acid.

In some cases, a chimeric Cas9 protein includes a heterologous polypeptide that has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other cases, a chimeric Cas9 protein includes a heterologous polypeptide that has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologs from a wide variety of species have been identified and in some cases the proteins share only a few identical amino acids. Identified Cas9 orthologs have similar domain architecture with a central HNH endonuclease domain and a split RuvC/RNaseH domain (e.g., RuvCI, RuvCII, and RuvCIII) (e.g., see Table 1). For example, a Cas9 protein can have 3 different regions (sometimes referred to as RuvC-I, RuvC-II, and RucC-III), that are not contiguous with respect to the primary amino acid sequence of the Cas9 protein, but fold together to form a RuvC domain once the protein is produced and folds. Thus, Cas9 proteins can be said to share at least 4 key motifs with a conserved architecture. Motifs 1, 2, and 4 are RuvC like motifs while motif 3 is an HNH-motif. The motifs set forth in Table 1 may not represent the entire RuvC-like and/or HNH domains as accepted in the art, but Table 1 does present motifs that can be used to help determine whether a given protein is a Cas9 protein.

In some cases, a suitable Cas9 protein includes an amino acid sequence having 60% or more, 70% or more, 75% or more, 80% or more, 85% or more, 90% or more, 95% or more, 99% or more or 100% amino acid sequence identity to the Cas9 amino acid sequence set forth in SEQ ID NO: 5, or to any of the amino acid sequences set forth as SEQ ID NOs: 6-263, and 265-816.

In some cases, a Cas9 protein includes 4 motifs (as listed in Table 1), at least one with (or each with) amino acid sequences having 75% or more, 80% or more, 85% or more, 90% or more, 95% or more, 99% or more or 100% amino acid sequence identity to each of the 4 motifs listed in Table 1 (SEQ ID NOs:1-4), or to the corresponding portions in any of the amino acid sequences set forth as SEQ ID NOs: 6-263, and 265-816.

As used herein, the term "Cas9 protein" encompasses a "chimeric Cas9 protein." As used herein, the term "Cas9 protein" encompasses a variant Cas9 that is a nickase. As used herein, the term "Cas9 protein" encompasses a variant Cas9 that exhibits reduced enzymatic activity.

TABLE 1

Table 1 lists 4 motifs that are present in Cas9 sequences from various species. The amino acids listed in Table 1 are from the Cas9 from *S. pyogenes* (SEQ ID NO: 5).

| Motif # | Motif | Amino acids (residue #s) | Highly conserved |
|---|---|---|---|
| 1 | RuvC-like I | IGLDIGTNSVGWAVI (7-21) (SEQ ID NO: 1) | D10, G12, G17 |
| 2 | RuvC-like II | IVIEMARE (759-766) (SEQ ID NO: 2) | E762 |
| 3 | HNH-motif | DVDHIVPQSFLKDDSIDNKVLTRSDKN (837-863) (SEQ ID NO: 3) | H840, N854, N863 |
| 4 | RuvC-like II | HHAHDAYL (982-989) (SEQ ID NO: 4) | H982, H983, A984, D986, A987 |

In some cases, a suitable Cas9 protein comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 as set forth in SEQ ID NOs: 1-4, respectively (e.g., see Table 1), or to the corresponding portions in any of the amino acid sequences set forth in SEQ ID NOs: 5-263, and 265-816.

In other words, in some cases, a suitable Cas9 polypeptide includes an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth in SEQ ID NO: 5 (e.g., the sequences set forth in SEQ ID NOs: 1-4, e.g., see Table 1), or to the corresponding portions in any of the amino acid sequences set forth in SEQ ID NOs: 6-263, and 265-816.

In some cases, a suitable Cas9 protein includes an amino acid sequence having 60% or more, 70% or more, 75% or more, 80% or more, 85% or more, 90% or more, 95% or more, 99% or more or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-263, and 265-816.

Any Cas9 protein as defined above can be used as a Cas9 polypeptide, as part of a chimeric Cas9 polypeptide (e.g., a Cas9 fusion protein), any of which can be used in an RNP of the present disclosure.

Variant Cas9 Proteins Nickases

In some cases, a Cas9 protein is a variant Cas9 protein. A variant Cas9 protein has an amino acid sequence that is different by at least one amino acid (e.g., has a deletion, insertion, substitution, fusion) when compared to the amino acid sequence of a corresponding wild type Cas9 protein. In some instances, the variant Cas9 protein has an amino acid change (e.g., deletion, insertion, or substitution) that reduces the nuclease activity of the Cas9 protein. For example, in some instances, the variant Cas9 protein has 50% or less, 40% or less, 30% or less, 20% or less, 10% or less, 5% or less, or 1% or less of the nuclease activity of the corresponding wild-type Cas9 protein. A protein (e.g., a class 2 CRISPR/Cas protein, e.g., a Cas9 protein) that cleaves one strand but not the other of a double stranded target nucleic acid is referred to herein as a "nickase" (e.g., a "nickase Cas9").

In some cases, a variant Cas9 protein can cleave the complementary strand (sometimes referred to in the art as the target strand) of a target nucleic acid but has reduced ability to cleave the non-complementary strand (sometimes referred to in the art as the non-target strand) of a target nucleic acid. For example, the variant Cas9 protein can have a mutation (amino acid substitution) that reduces the function of the RuvC domain. Thus, the Cas9 protein can be a nickase that cleaves the complementary strand, but does not cleave the non-complementary strand. As a non-limiting example, in some embodiments, a variant Cas9 protein has a mutation at an amino acid position corresponding to residue D10 (e.g., D10A, aspartate to alanine) of SEQ ID NO: 5 (or the corresponding position of any of the proteins set forth in SEQ ID NOs: 6-261 and 265-816) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 protein cleaves a double stranded target nucleic acid) (see, for example, Jinek et al., Science. 2012 Aug. 17; 337(6096):816-21). See, e.g., SEQ ID NO: 262.

In some cases, a variant Cas9 protein can cleave the non-complementary strand of a target nucleic acid but has reduced ability to cleave the complementary strand of the target nucleic acid. For example, the variant Cas9 protein can have a mutation (amino acid substitution) that reduces the function of the HNH domain. Thus, the Cas9 protein can be a nickase that cleaves the non-complementary strand, but does not cleave the complementary strand. As a non-limiting example, in some embodiments, the variant Cas9 protein has a mutation at an amino acid position corresponding to residue H840 (e.g., an H840A mutation, histidine to alanine) of SEQ ID NO: 5 (or the corresponding position of any of the proteins set forth as SEQ ID NOs: 6-261 and 265-816) and can therefore cleave the non-complementary strand of the target nucleic acid but has reduced ability to cleave (e.g., does not cleave) the complementary strand of the target nucleic acid. Such a Cas9 protein has a reduced ability to cleave a target nucleic acid (e.g., a single stranded target nucleic acid) but retains the ability to bind a target nucleic acid (e.g., a single stranded target nucleic acid). See, e.g., SEQ ID NO: 263.

Other residues can be mutated to achieve the above effects (i.e. inactivate one or the other nuclease portions). As non-limiting examples, residues D10, G12, G17, E762, H840, N854, N863, H982, H983, A984, D986, and/or A987 of SEQ ID NO: 5 (or the corresponding mutations of any of the proteins set forth as SEQ ID NOs: 6-261, and 265-816) can be altered (i.e., substituted), with the proviso that D10 and H840 are not mutated in the same protein. Also, mutations other than alanine substitutions are suitable.

In some embodiments, a variant Cas9 protein that has reduced catalytic activity (e.g., when a Cas9 protein has a D10, G12, G17, E762, H840, N854, N863, H982, H983, A984, D986, and/or a A987 mutation of SEQ ID NO: 5 or the corresponding mutations of any of the proteins set forth as SEQ ID NOs: 6-263, and 265-816, e.g., D10A, G12A, G17A, E762A, H840A, N854A, N863A, H982A, H983A, A984A, and/or D986A), the variant Cas9 protein can still bind to target nucleic acid in a site-specific manner (because it is still guided to a target nucleic acid sequence by a Cas9 guide RNA) as long as it retains the ability to interact with the Cas9 guide RNA.

In addition to the above, a variant Cas9 protein can have the same parameters for sequence identity as described above for Cas9 proteins. Thus, in some cases, a suitable variant Cas9 protein includes an amino acid sequence having 4 motifs, each of motifs 1-4 having 60% or more, 70% or more, 75% or more, 80% or more, 85% or more, 90% or more, 95% or more, 99% or more or 100% amino acid sequence identity to motifs 1-4 of the Cas9 amino acid sequence set forth as SEQ ID NO: 5 (the motifs are in Table 1, below, and are set forth as SEQ ID NOs: 1-4, respectively), or to the corresponding portions in any of the amino acid sequences set forth in SEQ ID NOs: 6-263, and 265-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to amino acids 7-166 or 731-1003 of the Cas9 amino acid sequence set forth in SEQ ID NO: 5, or to the corresponding portions in any of the amino acid sequences set forth as SEQ ID NOs: 6-263, and 265-816.

In some cases, a suitable variant Cas9 protein comprises an amino acid sequence having 60% or more, 70% or more, 75% or more, 80% or more, 85% or more, 90% or more, 95% or more, 99% or more, or 100% amino acid sequence identity to the Cas9 amino acid sequence set forth in SEQ ID NO: 5, or to any of the amino acid sequences set forth as SEQ ID NOs: 6-263, and 265-816.

Type V and Type VI CRISPR/Cas Endonucleases

In some cases, a coding sequence(s) of the present functional nucleic acid encodes a type V or type VI CRISPR/Cas endonuclease (i.e., the sequence-specific, e.g., genome editing, endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonucelase. Examples of type V CRISPR/Cas endonucleases include but are not limited to: Cpf1, C2c1, and C2c3. An example of a type VI CRISPR/Cas endonuclease is C2c2. In some cases, a sequence-specific endonuclease includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., C2c2).

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art, for example, see Zetsche et al, Cell. 2015 Oct. 22; 163(3):759-71; Makarova et al, Nat Rev Microbiol. 2015 November; 13(11):722-36; and Shmakov et al., Mol Cell. 2015 Nov. 5; 60(3):385-97.

In some cases, the Type V or type VI CRISPR/Cas endonuclease (e.g., Cpf1, C2c1, C2c2, C2c3) is enzymatically active, e.g., the Type V or type VI CRISPR/Cas polypeptide, when bound to a guide RNA, cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein. In some cases, a Cpf1 protein includes an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092. In some cases, a Cpf1 protein includes an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the Cpf1 amino acid sequence set forth in any of SEQ ID NOs: 1088-1092.

In some cases, a Cpf1 protein includes an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the Cpf1 amino acid sequence set forth in any of SEQ ID NOs: 1088-1092. In some cases, a Cpf1 protein includes an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the Cpf1 amino acid sequence set forth in any of SEQ ID NOs: 1088-1092. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the Cpf1 amino acid sequence set forth in any of SEQ ID NOs: 1088-1092.

In some cases, the Cpf1 protein exhibits reduced enzymatic activity relative to a wild-type Cpf1 protein (e.g., relative to a Cpf1 protein comprising the amino acid sequence set forth in any of SEQ ID NOs: 1088-1092), and retains DNA binding activity. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 917 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., an E→A substitution) at an amino acid residue corresponding to amino acid 1006 of the Cpf1 amino acid sequence set forth in SEQ ID NO: 1088. In some cases, a Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092; and comprises an amino acid substitution (e.g., a D→A substitution) at an amino acid residue corresponding to amino acid 1255 of the Cpf1 amino acid sequence set forth in SEQ ID NO: 1088.

In some cases, a suitable Cpf1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the Cpf1 amino acid sequence set forth in any of SEQ ID NOs: 1088-1092.

In some cases a type V CRISPR/Cas endonuclease is a C2c1 protein (examples include those set forth as SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c1 amino acid sequence set forth in any of SEQ ID NOs: 1112-1119.

In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c1 amino acid sequences set forth in any of SEQ ID NOs: 1112-1119). In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c1 amino acid sequence set forth in any of SEQ ID NOs: 1112-1119. In some cases, a C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c1 amino acid sequence set forth in any of SEQ ID NOs: 1112-1119.

In some cases, the C2c1 protein exhibits reduced enzymatic activity relative to a wild-type C2c1 protein (e.g., relative to a C2c1 protein comprising the amino acid sequence set forth in any of SEQ ID NOs: 1112-1119), and retains DNA binding activity. In some cases, a suitable C2c1 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c1 amino acid sequence set forth in any of SEQ ID NOs: 1112-1119.

In some cases a type V CRISPR/Cas endonuclease is a C2c3 protein (examples include those set forth as SEQ ID NOs: 1120-1123). In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c3 amino acid sequence set forth in any of SEQ ID NOs: 1120-1123.

In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c3 amino acid sequence set forth in any of SEQ ID NOs: 1120-1123. In some cases, a C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c3 amino acid sequence set forth in any of SEQ ID NOs: 1120-1123.

In some cases, the C2c3 protein exhibits reduced enzymatic activity relative to a wild-type C2c3 protein (e.g., relative to a C2c3 protein comprising the amino acid sequence set forth in any of SEQ ID NOs: 1120-1123), and retains DNA binding activity. In some cases, a suitable C2c3 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c3 amino acid sequence set forth in any of SEQ ID NOs: 1120-1123.

In some cases a type VI CRISPR/Cas endonuclease is a C2c2 protein (examples include those set forth as SEQ ID NOs: 1124-1135). In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to a contiguous stretch of from 100 amino acids to 200 amino acids (aa), from 200 aa to 400 aa, from 400 aa to 600 aa, from 600 aa to 800 aa, from 800 aa to 1000 aa, from 1000 aa to 1100 aa, from 1100 aa to 1200 aa, or from 1200 aa to 1300 aa, of the C2c2 amino acid sequence set forth in any of SEQ ID NOs: 1124-1135.

In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCIII domain of the C2c2 amino acid sequence set forth in any of SEQ ID NOs: 1124-1135. In some cases, a C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the RuvCI, RuvCII, and RuvCIII domains of the C2c2 amino acid sequence set forth in any of SEQ ID NOs: 1124-1135.

In some cases, the C2c2 protein exhibits reduced enzymatic activity relative to a wild-type C2c2 protein (e.g., relative to a C2c2 protein comprising the amino acid sequence set forth in any of SEQ ID NOs: 1124-1135), and retains DNA binding activity. In some cases, a suitable C2c2 protein comprises an amino acid sequence having at least 30%, at least 35%, at least 40%, at least 45%, at least 50%, at least 55%, at least 60%, at least 65%, at least 70%, at least 75%, at least 80%, at least 85%, at least 90%, at least 95%, at least 90%, or 100%, amino acid sequence identity to the C2c2 amino acid sequence set forth in any of SEQ ID NOs: 1124-1135.

Guide RNA (for CRISPR/Cas Endonucleases)

A nucleic acid molecule that binds to a class 2 CRISPR/Cas endonuclease (e.g., a Cas9 protein; a type V or type VI CRISPR/Cas protein; a Cpf1 protein; etc.) and targets the complex to a specific location within a target nucleic acid is referred to herein as a "guide RNA" or "CRISPR/Cas guide nucleic acid" or "CRISPR/Cas guide RNA."

A guide RNA provides target specificity to the complex (the RNP complex) by including a targeting segment, which includes a guide sequence (also referred to herein as a targeting sequence), which is a nucleotide sequence that is complementary to a sequence of a target nucleic acid.

A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules: an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides), and the guide RNA is referred to as a "single guide RNA", a "single-molecule guide RNA," a "one-molecule guide RNA", or simply "sgRNA."

Cas9 Guide RNA

A nucleic acid molecule that binds to a Cas9 protein and targets the complex to a specific location within a target nucleic acid is referred to herein as a "Cas9 guide RNA."

A Cas9 guide RNA (can be said to include two segments, a first segment (referred to herein as a "targeting segment"); and a second segment (referred to herein as a "protein-binding segment"). By "segment" it is meant a segment/section/region of a molecule, e.g., a contiguous stretch of nucleotides in a nucleic acid molecule. A segment can also mean a region/section of a complex such that a segment may comprise regions of more than one molecule.

The first segment (targeting segment) of a Cas9 guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a Cas9 polypeptide. The protein-binding segment of a subject Cas9 guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid.

A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g. a target sequence in a chromosomal nucleic acid, e.g., a chromosome; a target sequence in an extrachromosomal nucleic acid, e.g. an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a Cas9 guide RNA can be modified so that the Cas9 guide RNA can target a Cas9 protein to any desired sequence of any desired target nucleic acid, with the exception that the protospacer adjacent motif (PAM) sequence is taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

A Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). The targeter molecule additionally provides the targeting segment. Thus, a targeter and an activator molecule (as a corresponding pair) hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA:"trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

A Cas9 guide RNA can also be said to include 3 parts: (i) a targeting sequence (a nucleotide sequence that hybridizes with a sequence of the target nucleic acid); (ii) an activator sequence (as described above)(in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g. a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

A Cas9 guide RNA (e.g. a dual guide RNA or a single guide RNA) can be comprised of any corresponding activator and targeter pair. Non-limiting examples of nucleotide sequences that can be included in a Cas9 guide RNA (dgRNA or sgRNA) include sequences set forth in SEQ ID NOs: 827-1075, or complements thereof. For example, in some cases, sequences from SEQ ID NOs: 827-957 (which are from tracrRNAs) or complements thereof, can pair with sequences from SEQ ID NOs: 964-1075 (which are from crRNAs), or complements thereof, to form a dsRNA duplex of a protein binding segment.

Targeting Segment of a Cas9 Guide RNA

The first segment of a subject guide nucleic acid includes a guide sequence (i.e., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

The targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

The percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Examples of various Cas9 proteins and Cas9 guide RNAs (as well as information regarding requirements related to protospacer adjacent motif (PAM) sequences present in targeted nucleic acids) can be found in the art, for example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4): 910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al., Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et al., Nat Methods. 2013 October; 10(10):957-63; Nakayama et al., Genesis. 2013 December; 51(12):835-43; Ran et al., Nat Protoc. 2013 November; 8(11):2281-308; Ran et at, Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Guide RNAs Corresponding to Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

A type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex).

The target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

The guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

The guide sequence of a type V or type VI CRISPR/Cas guide RNA (e.g., Cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

The duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an example, a duplex-forming segment of a Cpf1 guide RNA can comprise a nucleotide sequence selected from (5' to 3'): AAUUUCUACUGUUGUAGAU (SEQ ID NO: 1093), AAUUUCUGCUGUUGCAGAU (SEQ ID NO: 1094), AAUUUCCACUGUUGUGGAU (SEQ ID NO: 1095), AAUUCCUACUGUUGUAGGU (SEQ ID NO: 1096), AAUUUCUACUAUUGUAGAU (SEQ ID NO: 1097), AAUUUCUACUGCUGUAGAU (SEQ ID NO: 1098), AAUUUCUACUUUGUAGAU (SEQ ID NO: 1099), and AAUUUCUACUUGUAGAU (SEQ ID NO: 1100). The guide sequence can then follow (5' to 3') the duplex forming segment.

A non-limiting example of an activator RNA (e.g. tracrRNA) of a C2c1 guide RNA (dual guide or single guide) is an RNA that includes the nucleotide sequence GAAUUUUUCAACGGGUGUGCCAAUGGCCAC-UUUCCAGGUGGCAAAGCCCGUUGA GCUUCU-CAAAAAG (SEQ ID NO: 1101). In some cases, a C2c1 guide RNA (dual guide or single guide) is an RNA that includes the nucleotide sequence In some cases, a C2c1 guide RNA (dual guide or single guide) is an RNA that includes the nucleotide sequence GUCUA-GAGGACAGAAUUUUUCAACGGGUGUGC-CAAUGGCCACUUUCCAGGUGGC AAAGCCCGUUGAGCUUCUCAAAAAG (SEQ ID NO: 1102). In some cases, a C2c1 guide RNA (dual guide or single guide) is an RNA that includes the nucleotide sequence UCUAGAGGACAGAAUUUUUCAACGGGU-GUGCCAAUGGCCACUUUCCAGGUGGCA AAGCCCGUUGAGCUUCUCAAAAAG (SEQ ID NO: 1103). A non-limiting example of an activator RNA (e.g. tracrRNA) of a C2c1 guide RNA (dual guide or single guide) is an RNA that includes the nucleotide sequence ACUUUCCAGGCAAAGCCCGUUGAGCUUCU-CAAAAAG (SEQ ID NO: 1104). In some cases, a duplex forming segment of a C2c1 guide RNA (dual guide or single guide) of an activator RNA (e.g. tracrRNA) includes the nucleotide sequence AGCUUCUCA (SEQ ID NO: 1105) or the nucleotide sequence GCUUCUCA (SEQ ID NO: 1106) (the duplex forming segment from a naturally existing tracrRNA.

A non-limiting example of a targeter RNA (e.g. crRNA) of a C2c1 guide RNA (dual guide or single guide) is an RNA with the nucleotide sequence CUGAGAAGUGGCACNNNNNNNNNNNNNNNNNNNN (SEQ ID NO: 1107), where the Ns represent the guide sequence, which will vary depending on the target sequence, and although 20 Ns are depicted a range of different lengths are acceptable. In some cases, a duplex forming segment of a C2c1 guide RNA (dual guide or single guide) of a targeter RNA (e.g. crRNA) includes the nucleotide sequence CUGAGAAGUGGCAC (SEQ ID NO: 1108) or includes the nucleotide sequence CUGAGAAGU (SEQ ID NO: 1109) or includes the nucleotide sequence UGAGAAGUGGCAC (SEQ ID NO: 1110) or includes the nucleotide sequence UGAGAAGU (SEQ ID NO: 1111).

Examples and guidance related to type V or type VI CRISPR/Cas endonucleases and guide RNAs (as well as information regarding requirements related to protospacer adjacent motif (PAM) sequences present in targeted nucleic acids) can be found in the art, for example, see Zetsche et al., Cell. 2015 Oct. 22; 163(3):759-71; Makarova et al., Nat Rev Microbiol. 2015 November; 13(11):722-36; and Shmakov et al., Mol Cell. 2015 Nov. 5; 60(3):385-97.

Recombinant Expression Vectors

Further aspects of the present disclosure include a recombinant expression vector that contains a functional nucleic acid of the present disclosure. The expression vector may be any suitable vector for delivering and expression of a nucleic acid contained therein to a host cell.

Vectors which may be used include, without limitation, lentiviral, herpes simplex virus, adenoviral, and adeno-associated virus (AAV) vectors. Lentiviral vectors include, but are not limited to human immunodeficiency virus (HIV)-based vectors. Lentiviral vectors may be pseudotyped with the envelope proteins of other viruses, including, but not limited to vesicular stomatitis virus (VSV), rabies, Mo-murine leukemia virus (MLV), baculovirus and Ebola. Such vectors may be prepared using standard methods in the art.

Other vectors of interest include plasmid vectors. The term plasmid as used herein can refer to nucleic acid, e.g., DNA derived from a plasmid vector, cosmid, phagemid or bacteriophage, into which one or more fragments of nucleic acid may be inserted or cloned which encode for particular genes. This includes the construction including extrachromosomal genetic material, usually of a circular duplex of DNA which can replicate independently of chromosomal DNA in a host cell.

A recombinant expression vector of the present disclosure may include one or more suitable regulatory sequences, e.g., promoters, as described above, to drive expression of the coding sequences in the present nucleic acid in a host cell of interest.

Recombinant Adeno-Associated Virus (rAAV) Virion

Also provided herein is a recombinant adeno-associated virus (rAAV) virion that includes an AAV capsid protein and a functional nucleic acid of the present disclosure. The functional nucleic acid may be part of any suitable expression vector, e.g., an AAV expression vector.

The AAV capsid protein may be any suitable capsid protein to deliver the functional nucleic acid to a host cell of interest. The AAV capsid may be of any suitable serotype (such as, but not limited to, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9)). The AAV capsid may be a wildtype capsid protein, or may be a variant AAV capsid protein that may have altered and/or enhanced tropism towards one or more cell types. Examples of suitable variant AAV capsid proteins are described in, e.g., WO 2012145601; US20120164106; and US20050053922, each of which are incorporated herein by reference.

An rAAV virion of the present disclosure may be an isolated rAAV virion, produced, isolated and purified using any suitable method.

Methods

Also provided herein is a method for providing a transient, sequence-specific endonuclease activity, e.g., a transient genome editing activity, in a target host cell. In general terms, a method of the present disclosure may include introducing a heterologous nucleic acid into a host cell, where the heterologous nucleic acid includes coding nucleotide sequence(s) encoding a sequence-specific endonuclease, as described above, and one or more endonuclease-recognized sequences. The heterologous nucleic acid introduced into the host cell may be configured to express the endonuclease in the host cell, e.g., by having one or more regulatory sequences operably coupled to the nucleotide sequence(s) encoding the sequence-specific endonuclease. The sequence-specific endonuclease may be engineered to target a nucleotide sequence in the host cell, e.g., a genomic nucleotide sequence. Thus, the sequence-specific endonuclease may provide a sequence-specific endonuclease activity that cleaves both the target sequence in the host genome, as well as the endonuclease-recognized sequences in the heterologous nucleic acid introduced into the host cell. The endonuclease-recognized sequences' are further positioned in the present heterologous nucleic acid such that cleavage by the sequence-specific endonuclease prevents further expression of the sequence-specific endonuclease from the cleaved heterologous nucleic acid. Thus, as more sequence-specific endonuclease is expressed from the nucleic acid, less heterologous nucleic acid remains intact to support further expression of the sequence-specific endonuclease.

In some cases, the total number of copies of the endonuclease-recognized sequences of the present heterologous nucleic in the host cell is greater than the number of target sites in the host cell. This may be due to introducing an amount of the heterologous nucleic acid that results in the number of copies of the endonuclease-recognized sequences of the present heterologous nucleic in the host cell being greater than the number of target sites in the host cell, or due to expansion of the number of copies of the heterologous nucleic acid in the host cell.

The rate at which the sequence-specific endonuclease activity provided by the present heterologous nucleic acid in a host cell is inactivated may vary, and may depend on many factors, such as promoter strength, number of copies of the heterologous nucleic acid introduced and/or generated in the cell, the catalytic activity of the sequence-specific endonuclease, the rate of cleavage of the host cell nucleic acid relative to the rate of cleavage of the heterologous nucleic acid (e.g., as determined by the sequence identity between the target sequence of the sequence-specific endonuclease and the nuclease-recognized sequence), rate of degradation of the sequence-specific endonuclease in the host cell, etc. Any one or combinations of these factors may be altered to control the rate of self-inactivation.

In some cases, the nuclease-recognized sequence includes one or more mismatches within the target sequence, as described above, such that the sequence-specific endonuclease will preferentially cleave the host target site over the heterologous nucleic acid, and in turn will preferentially cleave the heterologous nucleic acid over other non-specific sites in the host cell.

The present method may result in the amount of endonuclease in a host cell that contains the present functional nucleic acid being lower than the amount of endonuclease in an appropriate control cell (e.g., a cell of the same type as the host cell and into which a control nucleic acid that is comparable to the functional nucleic acid except for the lack of the nuclease-recognized sequences is introduced). The amount of endonuclease expressed in a host cell may be estimated by measuring, e.g., intensity of fluorescence emitted from a fluorescent moiety (such as a green fluorescent protein (GFP)) fused to the sequence-specific endonuclease in a cell.

The present method may result in the fraction of host cells expressing the endonuclease being lower than the fraction of control cells expressing the endonuclease (e.g., cells of the same type as the host cells and into which a control nucleic acid that is comparable to the functional nucleic acid except for the lack of the nuclease-recognized sequences is introduced). The fraction of endonuclease-expressing host cells may be quantitated by detecting, e.g., the presence of fluorescence emitted from a fluorescent moiety (such as a green fluorescent protein (GRFP)) fused to the sequence-specific endonuclease in the cell. In some embodiments, the fraction of host cells expressing the sequence-specific nuclease from the present functional nucleic acid is reduced by a factor of 10% or more, e.g., 20% or more, 30% or more, 40% or more, 50% or more, 60% or more, 65% or more, 70% or more, 75% or more, including 80% or more, and in some cases, is 100% or less, e.g., 95% or less, 90% or less, 85% or less, including 80% or less, compared to the fraction of controls cells expressing the sequence-specific nuclease from a nucleic acid that does not include the nuclease-recognized sequences. In some embodiments, the fraction of host cells expressing the sequence-specific nuclease from the present functional nucleic acid is reduced by a factor in the range of 10 to 100%, e.g., 20 to 95%, 30 to 90%, 40 to 90%, 50 to 90%, 60 to 90%, including 65 to 85%, compared to the fraction of controls cells expressing the sequence-specific nuclease from the a nucleic acid that does not include the nuclease-recognized sequences.

The reduction in the amount of the sequence-specific nuclease expressed in a host cell and/or fraction of host cells expressing the sequence-specific nuclease compared to an appropriate control may be observed 1 day or more, e.g., 2 days or more, 3 days or more, including 4 days or more after delivering the functional nucleic acid to the host cell, and in some cases may be observed 2 weeks or less, e.g., 1 week or less, 6 days or less, including 4 days or less after delivering the functional nucleic acid to the host cell. In some embodiments, the reduction in the amount of the sequence-specific nuclease is observed in 1 day to 2 weeks, e.g., 2 days to 1 week, 2 days to 6 days, including 3 days to 6 days.

A host nucleic acid, e.g., genomic DNA, that is cleaved at a target site by the present sequence-specific endonuclease may be repaired by non-homologous end joining (NHEJ) or by homology-directed repair (HDR), such as homologous recombination. As such, the presence of a second piece of nucleic acid that has arms that are sufficiently complementary to the cleaved ends of the host nucleic acid may induce homologous recombination between the second piece of nucleic acid and the host nucleic acid, resulting in incorporation of sequences in the second piece nucleic acid into the host nucleic acid. Thus, in some embodiments, the present method further includes introducing into the host cell a second heterologous nucleic acid that will undergo homologous recombination with the host nucleic acid.

A first or second heterologous nucleic acid of the present disclosure may be introduced into a host cell using any suitable method. In some cases, host cells can be contacted with vectors comprising the present heterologous nucleic acid encoding a sequence-specific, e.g., genome editing, endonuclease (e.g., a zinc finger nuclease, a TALEN, a class 2 CRISPR/Cas endonuclease, etc.) and/or a CRISPR/Cas guide RNA such that the vectors are taken up by the cells. Methods for contacting host cells with nucleic acid vectors that are plasmids, including electroporation, calcium chloride transfection, microinjection, and lipofection are well known in the art. For viral vector delivery, the host cells are contacted with viral particles comprising the nucleic acid. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the host cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct micro-injection (e.g., injection of RNA into a zebrafish embryo).

Suitable methods to introduce the heterologous nucleic acid into a host cell include, without limitation, viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et. al Adv Drug Deliv Rev. 2012 Sep. 13. pii: S0169-409X(12)00283-9. doi: 10.1016/j.addr.2012.09.023), and the like.

Host Cells

A target host cell may be any suitable cell. The host cell may be a eukaryotic cell, for example, a eukaryotic cell in vitro, a eukaryotic cell in vivo, or a eukaryotic cell ex vivo. Suitable host cells include, but are not limited to: a single-celled eukaryotic organism; a cell of a single-cell eukaryotic organism; a plant cell; an algal cell, e.g., *Botryococcus braunii*, *Chlamydomonas reinhardtii*, *Nannochloropsis gaditana*, *Chlorella pyrenoidosa*, *Sargassum patens, C. agardh*, and the like; a fungal cell (e.g., a yeast cell); an animal cell; a cell of an invertebrate animal (e.g. fruit fly, cnidarian, echinoderm, nematode, etc.); a cell of a vertebrate animal (e.g., fish, amphibian, reptile, bird, mammal); a cell of a mammal (e.g., a cell of a rodent such as a mouse or rat, a cell of a non-human primate, a cell of a human, etc.); and the like. Any type of cell may be of interest (e.g. a stem cell, e.g. an embryonic stem (ES) cell, an induced pluripotent stem (iPS) cell, a hematopoietic stem cell, a germ cell (e.g., an oocyte, a sperm, an oogonia, a spermatogonia, etc.), a somatic cell, e.g. a fibroblast, an oligodendrocyte, a glial cell, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some embodiments, the host cell include an in vivo host cell. Suitable host cells include retinal cells (e.g., Müller cells, ganglion cells, amacrine cells, horizontal cells, bipolar cells, and photoreceptor cells including rods and cones, Müller glial cells, and retinal pigmented epithelium); neural cells (e.g., cells of the thalamus, sensory cortex, zona incerta (ZI), ventral tegmental area (VTA), prefontal cortex (PFC), nucleus accumbens (NAc), amygdala (BLA), substantia nigra, ventral pallidum, globus pallidus, dorsal striatum, ventral striatum, subthalamic nucleus, hippocampus, dentate gyrus, cingulate gyrus, entorhinal cortex, olfactory cortex, primary motor cortex, or cerebellum); liver cells; kidney cells; immune cells (e.g., T cells, B cells, and the like); cardiac cells; skeletal muscle cells; smooth muscle cells; lung cells; and the like.

Systems

Also provided herein is a system, e.g., a self-inactivating genome editing system that includes a functional nucleic acid, as described herein, in a host cell, and a sequence-specific endonuclease expressed in the host cell from the functional nucleic acid. The sequence-specific endonuclease may be any suitable sequence-specific, e.g., genome editing, endonuclease, as described above. The sequence-specific endonuclease may be engineered such that a target sequence in a target site of the hosts genomic nucleic acid directs cleavage of genomic nucleic acid at the target site by the sequence-specific endonuclease, and endonuclease-recognized sequences in the functional nucleic acid direct cleavage, e.g., excision, of the functional nucleic acid by the sequence-specific endonuclease, to prevent further expression of the sequence-specific endonuclease from the cleaved functional nucleic acid, as described above.

The present system may in some cases include a second heterologous nucleic acid that can direct homologous recombination at a cleavage site of the sequence-specific endonuclease in the host genomic nucleic acid, to incorporate a heterologous sequence into the host genomic nucleic acid at the site of cleavage, as described above.

The present disclosure provides a self-inactivating genome editing system comprising: a) a functional nucleic acid comprising: i) a nucleotide sequence encoding an RNA-guided site-specific endonuclease; and ii) target nucleotide sequences flanking the RNA-guided site-specific endonuclease-encoding nucleotide sequence, wherein target nucleotide sequences are cleavable by the RNA-guided site-specific endonuclease; and b) a guide RNA. The present disclosure provides a self-inactivating genome editing system comprising: a) a functional nucleic acid comprising: i) a nucleotide sequence encoding an RNA-guided site-specific endonuclease; and ii) target nucleotide sequences flanking the RNA-guided site-specific endonuclease-encoding nucleotide sequence, wherein target nucleotide sequences are cleavable by the RNA-guided site-specific endonuclease; and b) a guide RNA that comprises: i) a DNA-targeting segment comprising a nucleotide sequence that is complementary to a nucleotide sequence in a target DNA; and ii) a protein-binding segment that interacts with the RNA-guided site-specific endonuclease. In some cases, the RNA-guided site-specific endonuclease-encoding nucleotide sequence is a Cas9 polynucleotide; and the guide RNA is a Cas9 guide RNA, which may be a single-guide RNA or a dual-guide RNA.

Utility

The present functional nucleic acids, and systems and methods of using the same, find use in various situations where transient expression of a sequence-specific endonuclease in a host cell is desired. In some aspects, the present disclosure provides a way to edit the genome of a host cell, e.g., to induce a double-stranded break (DSB) at a specific genomic location and generate a desired modification during subsequent DNA break repair, e.g., induce a insertion or deletion (indel) in a gene with aberrant activity to inactivate the gene; repair a mutation in a defective gene by homology directed repair, etc. As the endonuclease activity provided to a host cell by the present functional nucleic acid is transient, the present functional nucleic acids, and systems and methods of using the same, provide for genome editing with less accumulation of the sequence-specific nuclease in a host cell, resulting in reduced toxicity due to reduced frequency of off-target cleavage, and/or reduced risk of immune responses to the sequence-specific nuclease, compared to expression of a sequence-specific nuclease from a nucleic acid that is not self-inactivating, i.e., that does not include the endonuclease-recognized sequences.

Off-target cleavage may refer to cleavage of a target nucleic acid at a site that is not specific relative to the target sequence (e.g., specific binding sequence) of the sequence-specific endonuclease, or to cleavage of a non-target nucleic acid (e.g., a nucleic acid that does not include the target sequence of the sequence-specific endonuclease. In some embodiments, off-target cleavage may include cleavage of a target nucleic acid at a site that includes an off-target nucleotide sequence having less than 70%, e.g., 65% or less, 60% or less, 55% or less, 50% or less, 40% or less, 30% or less, 20% or less, including 10% or less sequence identity, or no sequence identity to the target sequence of the sequence-specific endonuclease.

In some embodiments, the present functional nucleic acids, and systems and methods of using the same provide for reduced cleavage of host cell nucleic acid, e.g., host genomic DNA, at off-target sites, compared to expression of the sequence-specific endonuclease from a nucleic acid that does not include endonuclease-recognized sequences. In some embodiments, the present functional nucleic acids, and systems and methods of using the same provide for reduced cleavage of host cell nucleic acid, e.g., host genomic DNA, at off-target sites by a factor of 10% or more, e.g., 20% or more, 30% or more, 40% or more, 50% or more, 60% or more, 70% or more, including 80% or more, and in some embodiments, by a factor of 99.9% or less, e.g., 99.5% or less, 99% or less, 95% or less, 90% or less, 85% or less, 80% or less, 75% or less, including 70% or less, compared to expression of the sequence-specific endonuclease from a nucleic acid that does not include endonuclease-recognized sequences. In some embodiments, the present functional nucleic acids, and systems and methods of using the same provide for reduced cleavage of host cell nucleic acid, e.g., host genomic DNA, at off-target sites by a factor in the range of 10 to 99.9%, e.g., 20 to 99.5%, 30 to 99%, 40 to 95%, including 50 to 90%, compared to expression of the sequence-specific endonuclease from a nucleic acid that does not include endonuclease-recognized sequences. In some cases, the present functional nucleic acids, and systems and methods of using the same provide for substantially no off-target cleavage of host cell nucleic acid, e.g., host genomic DNA. In some cases, the ratio of on-target to off-target cleavage of host cell nucleic acid (e.g., host genomic DNA), using a functional nucleic acid or system of the present disclosure, is at least 2:1, at least 5:1, at least 10:1, at least 25:1, at least 50:1, at least 100:1, or more than 100:1.

In some embodiments, the present functional nucleic acids, and systems and methods of using the same finds use in therapeutic applications for treating genetic disorders. In some embodiments, the genetic disorder is a recessive disorder due to loss-of-function mutations (such as, but not limited to, cystic fibrosis, sickle-cell anemia, hemophilia B, tyrosinemia, or Duchenne muscular dystrophy). In some cases, the genetic disorder is a dominant negative disorder due to a haploinsufficiency (such as, but not limited to, transthyretin-related hereditary amyloidosis or dominant forms of retinitis pigmentosum). In some cases, the genetic disorder is a disorder caused by duplication of genomic sequences (such as, but not limited to, Friedreich's ataxia).

In some embodiments, the present functional nucleic acids, and systems and methods of using the same finds use in therapeutic applications for reducing the risk of acquiring a disease or infection. In some embodiments, the disease or infection is, without limitation, human immune deficiency virus (HIV) infection (e.g., via inactivation of the CCR5 receptor in lymphocytes), or hypercholesterolemia or hyperlipidemia (e.g., via inactivation of PCSK9).

In some embodiments, the present functional nucleic acids, and systems and methods of using the same finds use in engineering therapeutic cells (such as, without limitation, engineered T cells for immunotherapy), which in turn can be used to treat a subject for cancer, autoimmune disease, etc.

Kits

Also provided herein is a kit containing a functional nucleic acid of the present disclosure. In some cases, the functional nucleic acid is part of an expression vector, as described herein. In some cases, the functional nucleic acid or the expression vector is included in a viral delivery vehicle, e.g., an rAAV virion, as described above. The kit may further include a suitable packaging to contain the functional nucleic acid (e.g., the expression vector or the rAAV virion containing the functional nucleic acid). The packaging may be any suitable container, including, but not limited to, vials, tubes, multi-well plates, etc. the packaging may be made of any suitable material, including plastic, glass, etc.

In some embodiments, the kit also includes a second heterologous nucleic acid that can direct homologous recombination at a cleavage site of the sequence-specific endonuclease in genomic nucleic acid of a host in which the functional nucleic acid is configured to express the sequence-specific endonuclease, to incorporate a heterologous sequence into the host genomic nucleic acid at the site of cleavage, as described above.

In some cases, the present kit includes instructions for using a functional nucleic acid of the present disclosure, including an expression vector or a viral delivery vehicle containing the functional nucleic acid. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, digital versatile disc (DVD), flash drive, Blue-ray Disc™ etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, the methods for obtaining the instructions are recorded on a suitable substrate.

Components of a subject kit can be in separate containers; or can be combined in a single container.

The present disclosure provides a kit comprising: a) a functional nucleic acid comprising: i) a nucleotide sequence encoding an RNA-guided site-specific endonuclease; and ii) target nucleotide sequences flanking the RNA-guided site-specific endonuclease-encoding nucleotide sequence, wherein target nucleotide sequences are cleavable by the RNA-guided site-specific endonuclease; and b) a guide RNA, or a nucleic acid comprising a nucleotide sequence encoding a guide RNA. The present disclosure provides a kit comprising: a) a functional nucleic acid comprising: i) a nucleotide sequence encoding an RNA-guided site-specific endonuclease; and ii) target nucleotide sequences flanking the RNA-guided site-specific endonuclease-encoding nucleotide sequence, wherein target nucleotide sequences are cleavable by the RNA-guided site-specific endonuclease; and b) a guide RNA that comprises: i) a DNA-targeting segment comprising a nucleotide sequence that is complementary to a nucleotide sequence in a target DNA; and ii) a protein-binding segment that interacts with the RNA-guided site-specific endonuclease. In some cases, the RNA-guided site-specific endonuclease-encoding nucleotide sequence is a Cas9 polynucleotide; and the guide RNA is a Cas9 guide RNA, which may be a single-guide RNA or a dual-guide RNA. Components of the kit can be in separate containers; or can be combined in a single container.

EXAMPLES

The following examples are put forth so as to provide those of ordinary skill in the art with a complete disclosure and description of how to make and use the disclosed subject matter, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: In Vitro Assay with Self-Inactivating Cas9 Fused to 2A-GFP Construct

Figure 3A:
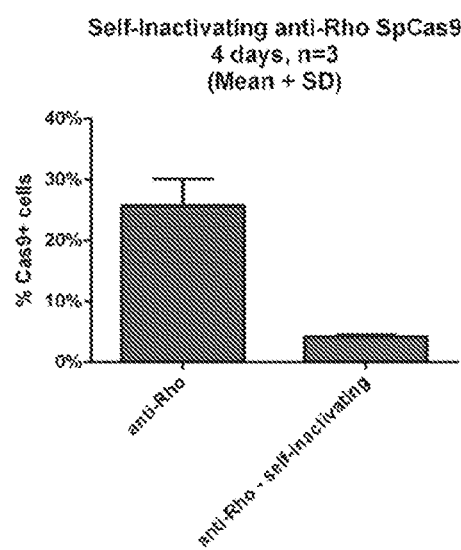
FIGS. 3A and 3B are a graph and an image showing in vitro self-inactivation of Cas9 fused to 2A-GFP, according to embodiments of the present disclosure.

A construct containing a Cas9 fused to 2A-GFP and a gRNA targeting Rho was introduced into cells, and the cells were cultured under standard conditions for 4 days. The construct containing the Rho targeting site inactivated its own expression as measured by GFP expression compared with non-inactivating Cas9-2A-GFP (FIG. 3A). A CEL-I Surveyor nuclease assay demonstrated that the self-inactivating Cas9 successfully cleaved DNA at a level comparable to non-inactivating Cas9 (FIG. 3B).

Figure 3B:
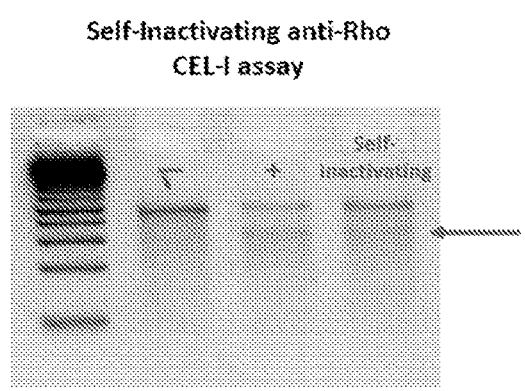

FIGS. 3A and 3B. (FIG. 3A) Percentage of GFP-expressing cells in cultures transfected with an expression construct for Cas9 fused to 2A-GFP, with or without the Rho targeting site. Error bars represent SEM. (FIG. 3B) Detection of Cas9-induced mutagenesis at the Rho locus using the CEL-I Surveyor nuclease assay. (−) negative control (no Cas9?); (+) Cas9 expressed from construct without Rho targeting site; (self-inactivating) Cas9 expressed from construct with Rho targeting site.

Example 2: Further Characterization of Self-Inactivating Cas9 Constructs

Dynamics of a Self-Inactivating Cas9 Constructs

Figure 4:
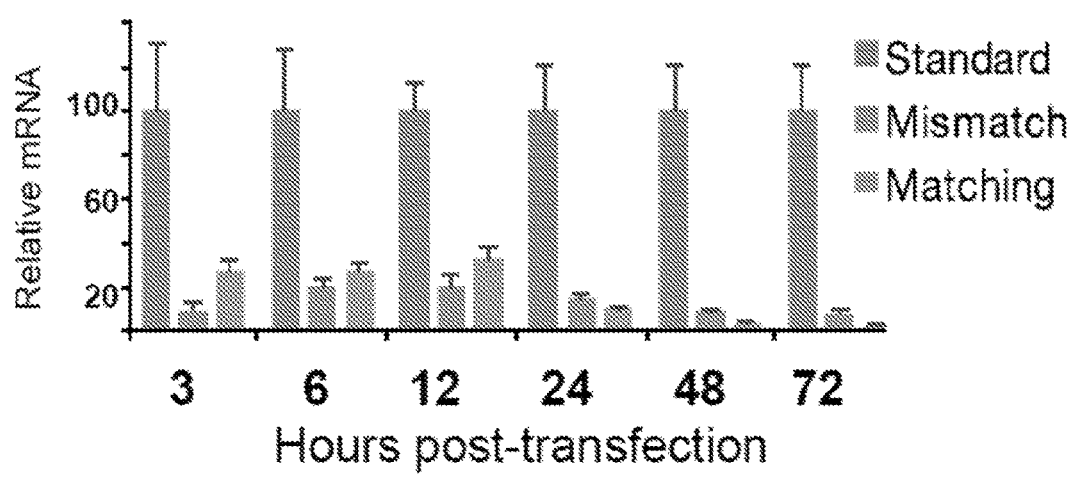
FIG. 4 depicts self-inactivating Cas9 construct dynamics.

HEK 293T cells were transfected with one of three variants of a vector comprising a nucleotide sequence encoding *Streptomyces pyogenes* Cas9 (SpCas9) and a guide RNA targeted to the gene encoding vascular endothelial growth factor A (VEGFA): normal vector; self-inactivating vector; or self-inactivating vector with mismatches. Cells were harvested at various time points (3 hours, 6 hours, 12 hours, 24 hours, 48 hours, or 72 hours post-transfection). Cellular mRNA was isolated from the harvested cells; the isolated mRNA was analyzed by reverse transcription-quantitative polymerase chain reaction (RT-qPCR). The results are shown in FIG. 4. While standard vector retained constant expression, perfectly matching self-inactivating vectors showed an increase in expression level until approximately 12 hours post-transfection, after which the expression levels drop, as the Cas9-encoding self-inactivating vector is eliminated. Variants comprising a mismatch in the incorporated target sites show similar, but slower, expression reduction, demonstrating tenability of self-inactivation.

Incorporating Mismatches into the Flanking Sites Restores On-Target Activity but not Off-Target Activity.

Figure 5A:
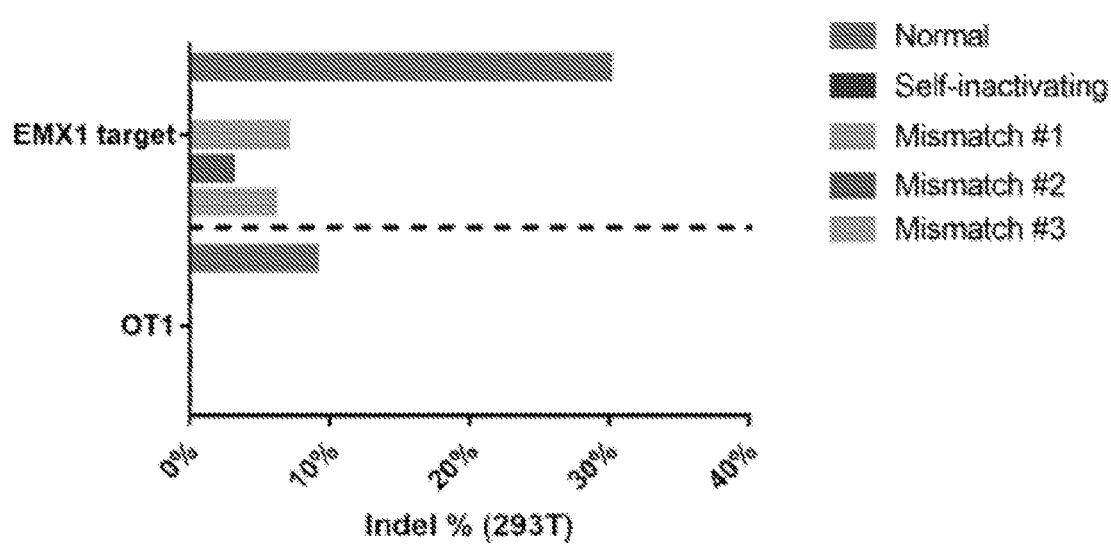
FIGS. 5A-5C depict the effect of mismatches in flanking sites on on-target activity and off-target activity.
Figure 5B:
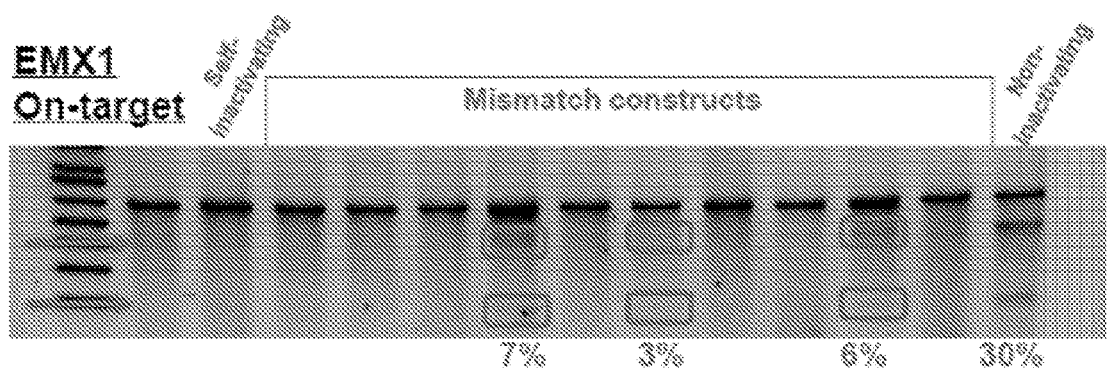
Figure 5C:
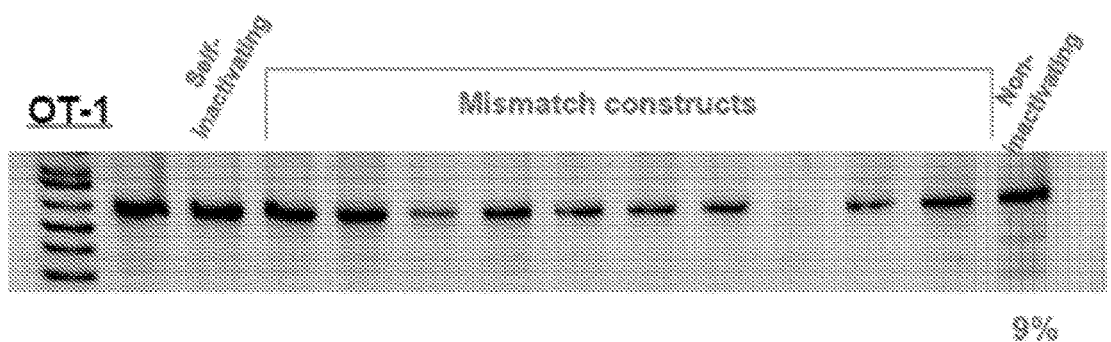

Normal and self-inactivating vectors comprising nucleotide sequences encoding *Staphylococcus aureus* Cas9 (SaCas9), targeted to the gene EMX1, were transfected into HEK-293T cells; genomic DNA was harvested from the cells 72 hours after transfection. The on-target site, and one established off-target site (EMX1-sg1 OT1) were amplified by PCR and analyzed using the T7 endonuclease I (T7EI) assay. PCR produces were melted, re-hybridized, and subjected to digestion with T7EI, cleaving mismatched duplex DNA. Cleavage bands detected on an agarose gel indicate hybrid PCR products of edited and unedited DNA, quantitatively demonstrating the presence of cells with an edited locus. The data are shown in FIGS. 5A-5C. The self-inactivating vector with no mismatches completely abolished both on-target and off-target activity. However, introduction of mismatches into the flanking self-inactivation sites restored partial on-target activity. Off-target activity was undetectable.

Self-Inactivating Cas9 Retained On-Target Activity and Reduced Off-Target Activity, Improving the On-Target/Off-Target Ratio.

Figure 6A:
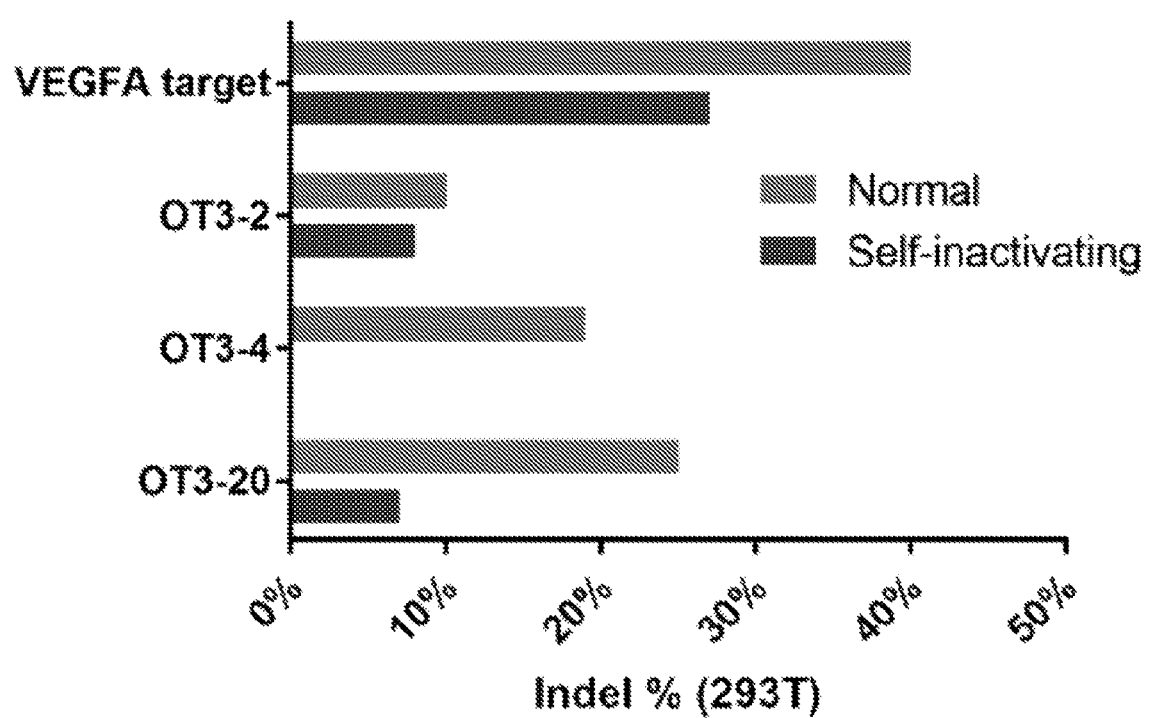
FIGS. 6A-6B depict on-target to off-target ratios of self-inactivating Cas9.
Figure 6B:
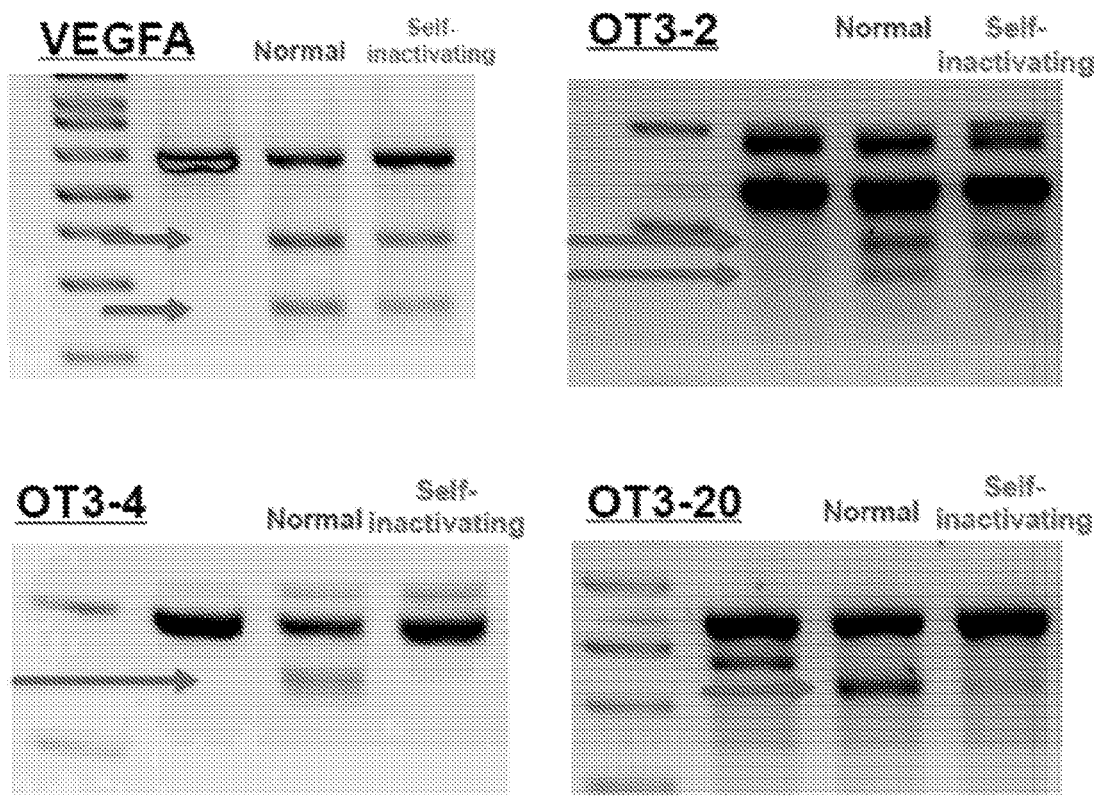

Normal and self-inactivating SpCas9 vectors targeted against VEGFA were transfected into HEK-293T cells. Genomic DNA was harvested after 72 hours. The on-target site and three established off-target sites (OT3-2, OT3-4, and OT3-20) were amplified by PCR and analyzed using the T7EI assay. The results are shown in FIGS. 6A-6B. Self-inactivating vectors showed somewhat decreased on-target activity but significantly improved on-target/off-target ratios in the T7EI assay. Self-inactivating vectors showed retention of most on-target activity. Self-inactivating vectors showed significantly reduced off-target activity at off-target OT3-2, undetectable off-target activity at off-target OT3-4, and less than 30% of normal off-target activity at off-target site OT3-20.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11530421B2). An electronic copy of the "Sequence Listing" will also be available from the USPTO upon request and payment of the fee set forth in 37 CFR 1.19(b)(3).

What is claimed is:

1. A recombinant expression vector comprising:
   i) a nucleotide sequence encoding a CRISPR-Cas endonuclease;
   ii) a regulatory element operably linked to the CRISPR-Cas endonuclease-encoding nucleotide sequence; and
   iii) flanking nucleotide sequences flanking the CRISPR-Cas endonuclease-encoding nucleotide sequence, wherein the flanking nucleotide sequences flanking the CRISPR-Cas endonuclease-encoding nucleotide sequence are cleavable by the CRISPR-Cas endonuclease when the CRISPR-Cas endonuclease is complexed with a guide RNA comprising: a) a CRISPR-Cas endonuclease binding segment that binds to the CRISPR-Cas endonuclease and b) a guide sequence that hybridizes to: (i) a target host nucleotide sequence in a target nucleic acid of a host cell; and (ii) the flanking nucleotide sequences,
   wherein each of the flanking nucleotide sequences has a length of 15 or more nucleotides and comprises: (i) 5 or fewer mismatches with the target host nucleotide sequence; or (ii) at least 70% sequence identity to the target host nucleotide sequence,
   wherein the recombinant expression vector is configured to express the CRISPR-Cas endonuclease in the host cell,
   and wherein cleavage of the recombinant expression vector by the CRISPR-Cas endonuclease complexed with the guide RNA reduces expression of the CRISPR-Cas endonuclease in the host cell.

2. The recombinant expression vector of claim 1, further comprising a nucleotide sequence encoding the guide RNA.

3. The recombinant expression vector of claim 1, wherein the guide RNA is a single-molecule guide RNA.

4. The recombinant expression vector of claim 1, wherein the regulatory element comprises a promoter and/or an enhancer.

5. The recombinant expression vector of claim 1, wherein each of the flanking nucleotide sequences comprises: (i) 3 or fewer mismatches with the target host nucleotide sequence; or (ii) at least 90% sequence identity to the target host nucleotide sequence.

6. The recombinant expression vector of claim 5, wherein each of the flanking nucleotide sequences has a length of 20 or more nucleotides.

7. The recombinant expression vector of claim 5, wherein the host cell target nucleic acid is in the host cell genome.

8. An isolated recombinant adeno-associated virus (rAAV) virion comprising:
   i) an AAV capsid protein; and
   ii) a recombinant expression vector of claim 1.

9. A method of cleaving a target nucleic acid in a host cell, the method comprising introducing into the host cell:
   1) a recombinant expression vector of claim 1 and
   2) a guide RNA, or a nucleic acid comprising a nucleotide sequence encoding the guide RNA, wherein the guide RNA comprises: a) a CRISPR-Cas endonuclease binding segment that binds to the CRISPR-Cas endonuclease; and b) a guide sequence that hybridizes to: (i) a target host nucleotide sequence in a target nucleic acid of a host cell; and (ii) the flanking nucleotide sequences, wherein:
   the CRISPR-Cas endonuclease, when complexed with the guide RNA, cleaves the host cell target nucleic acid.

10. The nucleic acid of claim 1, wherein the CRISPR-Cas endonuclease is Cas9 endonuclease.

11. The method of claim 9, wherein the CRISPR-Cas endonuclease is Cas9 endonuclease.

* * * * *

UNITED STATES PATENT AND TRADEMARK OFFICE
CERTIFICATE OF CORRECTION

PATENT NO. : 11,530,421 B2
APPLICATION NO. : 16/068011
DATED : December 20, 2022
INVENTOR(S) : Schaffer et al.

It is certified that error appears in the above-identified patent and that said Letters Patent is hereby corrected as shown below:

In the Specification

Please replace Column 4, Line 35, with the following:
--FIGS. 2A-2B are a collection of schematic diagrams--

Please replace Column 20, Line 43, with the following:
--of two FokI nuclease monomers, ZFNs generate a functional--

Please replace Column 22, Line 22, with the following:
--II restriction endonuclease such a FokI (see e.g., Kim et al.--

Signed and Sealed this
Nineteenth Day of December, 2023

Katherine Kelly Vidal
*Director of the United States Patent and Trademark Office*